(12) United States Patent
Melki et al.

(10) Patent No.: US 8,394,932 B2
(45) Date of Patent: Mar. 12, 2013

(54) SURVIVAL MOTOR NEURONS (SMN) GENE: A GENE FOR SPINAL MUSCULAR ATROPHY

(75) Inventors: Judith Melki, Paris (FR); Arnold Munnich, Paris (FR)

(73) Assignee: Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 13/096,574

(22) Filed: Apr. 28, 2011

(65) Prior Publication Data

US 2011/0294226 A1 Dec. 1, 2011

Related U.S. Application Data

(62) Division of application No. 11/603,305, filed on Nov. 22, 2006, which is a division of application No. 11/222,810, filed on Sep. 12, 2005, now abandoned, which is a division of application No. 09/109,082, filed on Jul. 2, 1998, now Pat. No. 7,033,752, which is a division of application No. 08/545,196, filed on Oct. 19, 1995, now Pat. No. 6,080,577.

(30) Foreign Application Priority Data

Oct. 19, 1994 (EP) .................................. 94402353

(51) Int. Cl.
*C07K 16/18* (2006.01)
(52) U.S. Cl. ................ 530/388.1; 530/387.9; 530/389.1
(58) Field of Classification Search .................. None
See application file for complete search history.

(56) References Cited

U.S. PATENT DOCUMENTS 7,033,752 B1 4/2006 Melki et al.

FOREIGN PATENT DOCUMENTS

WO WO 96/19566 * 6/1996

OTHER PUBLICATIONS

Lefebvre S et al. Identification and characterization of a spinal muscular atrophy-determining gene. Cell, Jan. 1995; 80:155-165.*
Padlan et al. Proc Natl Acad Sci USA, 1989; 86:5938-5942.*
Paul, WE. Fundamental Immunology, Third Edition, Raven Press, New York, 1993, pp. 292-295.*
Clermont et al., "Use of Genetic and Physical Mapping to Locate the Spinal Muscular Atrophy Locus between Two New Highly Polymorphic DNA Markers", Am. J. Hum. Genet., vol. 54 (1994) pp. 687-694.
Cross et al., Nature Genetics, vol. 6 (1994) pp. 236-244.
Das et al., J. of Biological Chemistry, vol. 260 (1985) pp. 6240-6247.
Frugier et al., "The molecular bases of spinal muscular atrophy", Current Opinion in Genetics and Development, vol. 12 (2002) pp. 294-298.
Melki et al., "De Novo and Inherited Deletions of the 5q13 Region in Spinal Muscular Atrophies", Science, vol. 264 (1994) p. 1474-1477.
Mickle et al., "Genotype-phenotype relationships in cystic fibrosis", Med. Clin. North Am., vol. 84, No. 3 (May 2000) pp. 597-607.
Rajeh et al., "Molecular analysis of the SMN and NAIP genes in Saudi spinal muscular atrophy patients", J. of Neurological Sciences, vol. 158 (1998) pp. 43-46.
Rudinger, Characteristics of the amino acids as components of a peptide hormone sequence, Peptide Hormones (Ed. J.A. Parsons), University Park Press (Baltimore, Md., 1976) pp. 1-7.
Stratagene Cloning Systems Catalog (1994), No. 300385, p. 103.
Stratagene Product Catalog (1991) p. 66.
The American Journal Human Genetics, vol. 55, No. 3, (Sep. 1994) A31.
Voet et al., Biochemistry, John Wiley & Sons, Inc., (1990) pp. 126-129 and 228-234.
Yan et al., "Two-amino acid molecular switch in an epithelial morphogen that regulates binding to two distinct receptors", Science, vol. 290 (2000) pp. 523-527.
Zapletalova et al., "Analysis of point mutations in the SMN1 gene in SMA patients bearing a single SMN1 copy", Neuromuscular Disorders, vol. 17 (2007) pp. 476-481.
Posters: Physical Mapping, A269, The American Journal of Human Genetics, Program and Abstracts 1994 Annual Meeting, vol. 55, No. 3, Sep. 1994.

* cited by examiner

*Primary Examiner* — Elizabeth C Kemmerer
*Assistant Examiner* — Kimberly A Ballard
(74) *Attorney, Agent, or Firm* — Birch, Stewart, Kolasch & Birch, LLP

(57) ABSTRACT

The present invention relates to the discovery of the human survival motor-neuron gene or SMD gene, which is a chromosome 5-SMA (Spinal Muscular Atrophy) determining gene. The present invention further relates to the nucleotide sequence encoding the SMN gene and corresponding amino acid sequence, a vector containing the gene encoding the SMN protein or a DNA sequence corresponding to the gene and transformant strains containing the SMN gene or a DNA sequence corresponding to the gene.

6 Claims, 20 Drawing Sheets

Figure 1

MAMSSGGSGGGVPEQEDSVLFRRGTGQSDDSDIWDDTALIKAYDKAVASFKHALKNG
DICETSGKPKTTPKRKPAKKNKSQKKNTAASLQQWKVGDKCSAIWSEDGCIYPATIA
SIDFKRETCVVVYTGYGNREEQNLSDLLSPICEVANNIEQNAQENENESQVSTDESE
NSRSPGNKSDNIKPKSAPWNSFLPPPPPMPGPRLGPGKPGLKFNGPPPPPPPPPHL
LSCWLPPFPSGPPIIPPPPPICPDSLDDADALGSMLISWYMSGYHTGYYMGFRQNQK
EGRCSHSLN

Figure 2A

CGGGGCCCCACGCTGCGCACCCGCGGGTTTGCTATGGCGATGAGCAGCGGCGGCAGT
GGTGGCGGCGTCCCGGAGCAGGAGGATTCCGTGCTGTTCCGGCGCGGCACAGGCCAG
AGCGATGATTCTGACATTTGGGATGATACAGCACTGATAAAAGCATATGATAAAGCT
GTGGCTTCATTTAAGCATGCTCTAAAGAATGGTGACATTTGTGAAACTTCGGGTAAA
CCAAAAACCACACCTAAAAGAAAACCTGCTAAGAAGAATAAAAGCCAAAAGAAGAAT
ACTGCAGCTTCCTTACAACAGTGGAAAGTTGGGGACAAATGTTCTGCCATTTGGTCA
GAAGACGGTTGCATTTACCCAGCTACCATTGCTTCAATTGATTTTAAGAGAGAAACC
TGTGTTGTGGTTTACACTGGATATGGAAATAGAGAGGAGCAAAATCTGTCCGATCTA
CTTTCCCCAATCTGTGAAGTAGCTAATAATATAGAACAGAATGCTCAAGAGAATGAA
AATGAAAGCCAAGTTTCAACAGATGAAAGTGAGAACTCCAGGTCTCCTGGAAATAAA
TCAGATAACATCAAGCCCAAATCTGCTCCATGGAACCCCTTTCTCCCTCCACCACCC
CCCATGCCAGGGCCAAGACTGGGACCAGGAAAGCCAGGTCTAAAATTCAATGGCCCA
CCACCGCCACCGCCACCACCACCACCCCACTTACTATCATGCTGGCTGCCTCCATTT
CCTTCTGGACCACCAATAATTCCCCCACCACCTCCCATATGTCCAGATTCTCTTGAT
GATGCTGATGCTTTGGGAAGTATGTTAATTTCATGGTACATGAGTGGCTATCATACT
GGCTATTATATGGGTTTTAGACAAAATCAAAAGAAGGAAGGTGCTCACATTCCTTA
AATTAAGGAGAAATGCTGGCATAGAGCAGCACTAAATGACACCACTAAAGAAACGAT
CAGACAGATCTGGAATGTGAAGCGTTATAGAAGATAACTGGCCTCATTTCTTCAAAA
TATCAAGTGTTGGGAAAGAAAAAAGGAAGTGGAATGGGTAACTCTTCTTGATTAAAA
GTTATGTAATAACCAAATGCAATGTGAAATATTTTACTGGACTCTTTTGAAAAACCA
TCTGTAAAAGACTGAGGTGGGGGTGGGAGGCCAGCACGGTGGTGAGGCAGTTGAGAA
AATTTGAATGTGGATTAGATTTTGAATGATATTGGATAATTATTGGTAATTTTATGG
CCTGTGAGAAGGGTGTTGTAGTTTATAAAAGACTGTCTTAATTTGCATACTTAAGCA
TTTAGGAATGAAGTGTTAGAGTGTCTTAAAATGTTTCAAATGGTTTAACAAAATGTA
TGTGAGGCGTATGTGGCAAAATGTTACAGAATCTAACTGGTGGACATGGCTGTTCAT
TGTACTGTTTTTTTCTATCTTCTATATGTTTAAAAGTATATAATAAAAATATTTAAT
TTTTTTTTAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAA

Figure 2B

AATTTTTAAATTTTTTGTAGAGACAGGGTCTCATTATGTTGCCCAGGGTGGTGTCAA
GCTCCAGGTCTCAAGTGATCCCCCTACCTCCGCCTCCCAAAGTTGTGGGATTGTAGG
CATGAGCCACTGCAAGAAACCTTAACTGCAGCCTAATAATTGTTTTCTTTGGGATA
ACTTTTAAAGTACATTAAAAGACTATCAACTTAATTTCTGATCATATTTTGTTGAAT
AAAATAAGTAAAATGTCTTGTGAACAAAATGCTTTTTAACATCCATATAAAGCTATC
TATATATAGCTATCTATATCTATATAGCTATTTTTTTTAACTTCCTTTTATTTTCCT
TACAG*GGTTTTAGACAAAATCAAAAAGAAGGAAGGTGCTCACATTCCTTAAATTAA
GGA*GTAAGTCTGCCAGCATTATGAAAGTGAATCTTACTTTTGTAAAACTTTATGGT
TTGTGGAAAACAAATGTTTTTGAACAGTTAAAAAGTTCAGATGTTAGAAAGTTGAAA
GGTTAATGTAAAACAATCAATATTAAAGAATTTTGATGCCAAAACTATTAGATAAAA
GGTTAATCTACATCCCTACTAGAATTCTCATACTTAACTGGTTGGTTGTGTGGAAGA
AACATACTTTCACAATAAAGAGCTTTAGGATATGATGCCATTTTATATCACTAGTAG
GCAGACCAGCAGACTTTTTTTATTGTGATATGGGATAACCTAGGCATACTGCACTG
TACACTCTGACATATGAAGTGCTCTAGTCAAGTTTAACTGGTGTCCACAGAGGACAT
GGTTTAACTGGAATTCGTCAAGCCTCTGGTTCTAATTTCTCATTTGCAG*GAAATGC
TGGCATAGAGCAGCACTAAATGACACCACTAAAGAAACGATCAGACAGATCTGGAAT
GTGAAGCGTTATAGAAGATAACTGGCCTCATTTCTTCAAAATATCAAGTGTTGGGAA
AGAAAAAAGGAAGTGGAATGGGTAACTCTTCTTGATTAAAAGTTATGTAATAACCAA
ATGCAATGTGAAATATTTTACTGGACTCTTTTGAAAAACCATCTGTAAAAGACTGAG
GTGGGGGTGGGAGGCCAGCACGGTGGTGAGGCAGTTGAGAAAATTTGAATGTGGATT
AGATTTTGAATGATATTGGATAATTATTGGTAATTTTATGGCCTGTGAGAAGGGTGT
TGTAGTTTATAAAAGACTGTCTTAATTTGCATACTTAAGCATTTAGGAATGAAGTGT
TAGAGTGTCTTAAAATGTTTCAAATGGTTTAACAAAATGTATGTGAGGCGTATGTGG
CAAAATGTTACAGAATCTAACTGGTGGACATGGCTGTTCATTGTACTGTTTTTTTCT
ATCTTCTATATGTTTAAAAGTATATAATAAAAATATTTAATTT

Figure 3A

1
CGGGGCCCCACGCTGCGCATCCGCGGGTTTGCTATGGCGATGAGCAGCGGCGGCAGT
GGTGGCGGCGTCCCGGAGCAGGAGGATTCCGTGCTGTTCCGGCGCGGCACAGGCAG
 2
*AGCGATGATTCTGACATTTGGGATGATACAGCACTGATAAAAGCATATGATAAAGC
TGTGGCTTCATTTAAGCATGCTCTAAAGAATGGTGACATTTGTGAAACTTCGGGTAA
ACCAAAAACCACACCTAAAAGAAAACCTGCTAAGAAGAATAAAAGCCAAAAGAAGAA
 3
TACTGCAGCTTCCTTACAACAG*TGGAAAGTTGGGGACAAATGTTCTGCCATTTGGT
CAGAAGACGGTTGCATTTACCCAGCTACCATTGCTTCAATTGATTTTAAGAGAGAAA
CCTGTGTTGTGGTTTACACTGGATATGGAAATAGAGAGGAGCAAAATCTGTCCGATC
 4
TACTTTCCCCAATCTGTGAAGTAGCTAATAATATAGAACAGAATGCTCAAGAG*AAT
GAAAATGAAAGCCAAGTTTCAACAGATGAAAGTGAGAACTCCAGGTCTCCTGGAAAT
AAATCAGATAACATCAAGCCCAAATCTGCTCCATGGAACTCTTTTCTCCCTCCACCA
 5
CCCCCCATGCCAGGGCCAAGACTGGGACCAGGAAAG*CCAGGTCTAAAATTCAATGG
CCCACCACCGCCACCGCCACCACCACCACCCCACTTACTATCATGCTGGCTGCCTCC
 6
ATTTCCTTCTGGACCACCA*ATAATTCCCCCACCACCTCCCATATGTCCAGATTCTC
TTGATGATGCTGATGCTTTGGGAAGTATGTTAATTTCATGGTACATGAGTGGCTATC
 7
ATACTGGCTATTATATG*GGTTTCAGACAAAATCAAAAGAAGGAAGGTGCTCACAT
 8
TCCTTAAATTAAGGA*GAAATGCTGGCATAGAGCAGCACTAAATGACACCACTAAAG
AAACGATCAGACAGATCTGGAATGTGAAGCGTTATAGAAGATAACTGGCCTCATTTC
TTCAAAATATCAAGTGTTGGGAAAGAAAAAAGGAAGTGGAATGGGTAACTCTTCTTG
ATTAAAAGTTATGTAATAACCAAATGCAATGTGAAATATTTACTGGACTCTTTTGA
AAAACCATCTGTAAAAGACTGGGGTGGGGGTGGGAGGCCAGCACGGTGGTGAGGCAG
TTGAGAAAATTTGAATGTGGATTAGATTTTGAATGATATTGGATAATTATTGGTAAT
TTTATGGCCTGTGAGAAGGGTGTTGTAGTTTATAAAGACTGTCTTAATTTGCATAC
TTAAGCATTTAGGAATGAAGTGTTAGAGTGTCTTAAAATGTTTCAAATGGTTTAACA
AAATGTATGTGAGGCGTATGTGGCAAAATGTTACAGAATCTAACTGGTGGACATGGC
TGTTCATTGTACTGTTTTTTCTATCTTCTATATGTTTAAAAGTATATAATAAAAAT
ATTTAATTTTTTTTTAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA

Figure 3B

AATTTTTAAATTTTTTGTAGAGACAGGGTCTCATTATGTTGCCCAGGGTGGTGTCAA
GCTCCAGGTCTCAAGTGATCCCCCTACCTCCGCCTCCCAAAGTTGTGGGATTGTAGG
CATGAGCCACTGCAAGAAAACCTTAACTGCAGCCTAATAATTGTTTTCTTTGGGATA
ACTTTTAAAGTACATTAAAAGACTATCAACTTAATTTCTGATCATATTTTGTTGAAT
AAAATAAGTAAAATGTCTTGTGAACAAAATGCTTTTTAACATCCATATAAAGCTATC
TATATATAGCTATCTATGTCTATATAGCTATTTTTTTAACTTCCTTTTATTTTCCT
TACAG*GGTTTCAGACAAAATCAAAAAGAAGGAAGGTGCTCACATTCCTTAAATTAA
GGA*GTAAGTCTGCCAGCATTATGAAAGTGAATCTTACTTTTGTAAAACTTTATGGT
TTGTGGAAAACAAATGTTTTTGAACAGTTAAAAAGTTCAGATGTTAAAAAGTTGAAA
GGTTAATGTAAAACAATCAATATTAAAGAATTTTGATGCCAAAACTATTAGATAAAA
GGTTAATCTACATCCCTACTAGAATTCTCATACTTAACTGGTTGGTTATGTGGAAGA
AACATACTTTCACAATAAAGAGCTTTAGGATATGATGCCATTTTATATCACTAGTAG
GCAGACCAGCAGACTTTTTTTTATTGTGATATGGGATAACCTAGGCATACTGCACTG
TACACTCTGACATATGAAGTGCTCTAGTCAAGTTTAACTGGTGTCCACAGAGGACAT
GGTTTAACTGGAATTCGTCAAGCCTCTGGTTCTAATTTCTCATTTGCAG*GAAATGC
TGGCATAGAGCAGCACTAAATGACACCACTAAAGAAACGATCAGACAGATCTGGAAT
GTGAAGCGTTATAGAAGATAACTGGCCTCATTTCTTCAAAATATCAAGTGTTGGGAA
AGAAAAAGGAAGTGGAATGGGTAACTCTTCTTGATTAAAAGTTATGTAATAACCAA
ATGCAATGTGAAATATTTTACTGGACTCTTTTGAAAAACCATCTGTAAAAGACTGGG
GTGGGGGTGGGAGGCCAGCACGGTGGTGAGGCAGTTGAGAAAATTTGAATGTGGATT
AGATTTTGAATGATATTGGATAATTATTGGTAATTTTATGGCCTGTGAGAAGGGTGT
TGTAGTTTATAAAAGACTGTCTTAATTTGCATACTTAAGCATTTAGGAATGAAGTGT
TAGAGTGTCTTAAAATGTTTCAAATGGTTTAACAAAATGTATGTGAGGCGTATGTGG
CAAAATGTTACAGAATCTAACTGGTGGACATGGCTGTTCATTGTACTGTTTTTTTCT
ATCTTCTATATGTTTAAAAGTATATAATAAAAATATTTAATTT

ACCTGANCCCAGANGGTCAAGGCTGCAGTGAGACGAGATTGCNCCACTGCCCTCCAC
CCTGGGTGATAAGAGTGGGACCCTGTNTCAAAACATACACACACACACACACACA
CACACACACACACACACACTCTCTCTCTCTCTCTCTCTCTCTCTCTCTCTCTCTC
TCTCTCTCAAAAACACTTGGTCTGTTATTTTTNCGAAATTGTCAGTCATAGTTATCT
GTTAGACCAAAGCTGNGTAAGNACATTTATTACATTGCCTCCTACAACTTCATCAGC
TAATGTATTTGCTATATAGCAATTACATATNGGNATATATTATCTTNAGGGGATGGC
CANGTNATAAAACTGTCACTGAGGAAAGGA

C272

CCTCCCACCTNAGCCTCCCCAGTAGCTAGGACTATAGGCGTGCNCCACCAAGCTCAG
CTATTTTTTNNTATTTAGTAGAGACGGGGTTTCGGCANGCTTAGGCCTCGTNTCGAAC
TCCAGTGTGTGTGTGTGTGTGTGTGTGTGTGTGTGTGTGTGTGTGTGTGTGTGTA
GATATTTATTCCCCCTCCCCCTTGGAAAAGTAAGTAAGCTCCTACTAGGAATTTAAA
ACCTGCTTGATCTATATAAAGACAAACAAGGAAAGACAAACATGGGGGCAGGAAGGA
AGGCAGATC

AFM157xd10

TCGAGGTAGATTTGTATTATATCCCATGTACACACACACACACACACACACACACAC
ACACACACAGACTTAATCTGTTTACAGAAATAAAAGGAATAAAATACCGTTTCTA
CTATACACCAAAACTAGCCATCTTGAC

C161

CCCTGAGAAGGCTTCCTCCTGAGTATGCATAAACATTCACAGCTTGCATGCGTGTGT
GTGTGTGTGTGTGTATGTTTGCTTGCACTGTAAAAACAATTGCAACATCAACA
GAAATAAAAATTAAAGGAATAATTCTCCTCCGACTCTGCCGTTCCATCCAGTGAAAC
TCTTCATTCTGGGGTAAAGTTCCTTCAGTTCTTTCATAGATAGGTATATACTTCATA
AGTCAAACAATCAGGCTGGGTGCAGTAGCTCATGCCTGTAATCCCAGCCCTTTGGGA
GGCCGAGCTGGGCAGATCGA

C171

TCCACCCGCCTTGGCCTCCCAAAGCNCTGGGATTACAGGCGTGACTGCCGCACCCAG
CTGTAAACTGGNTTNNTAATGGTAGATTTTNAGGTATTAACAATAGATAAAAGATA
CTTTTNGGCATACTGTGTATTGGGATGGGGTTAGAACAGGTGTNCTACCCAAGACAT
TTACTTAAAATCGCCCTCGAAATGCTATGTGAGCTGTGTGTGTGTGTGTGTGTGT
GTGTATTAAGGAAAAGCATGAAGTATTTATGCTTGATTTTTTTTTTNACTCATAG
CTTCATAGTGGANCAGATACATAGTCTAAATCAAAATGTTTAAACTTTTTATGTCAC

Restriction map of the 5q13 region for EagI(Ea), SacII(SacII), SfiII(Sfi). Numbers under parenthesis indicate the restriction fragment detected by He3; Telomeric element (E Tel), centromeric element (E cen), Centromer(Cent.), Telomere(Tel.). Probes are indicated above the restriction map. YACS are below the restriction map.

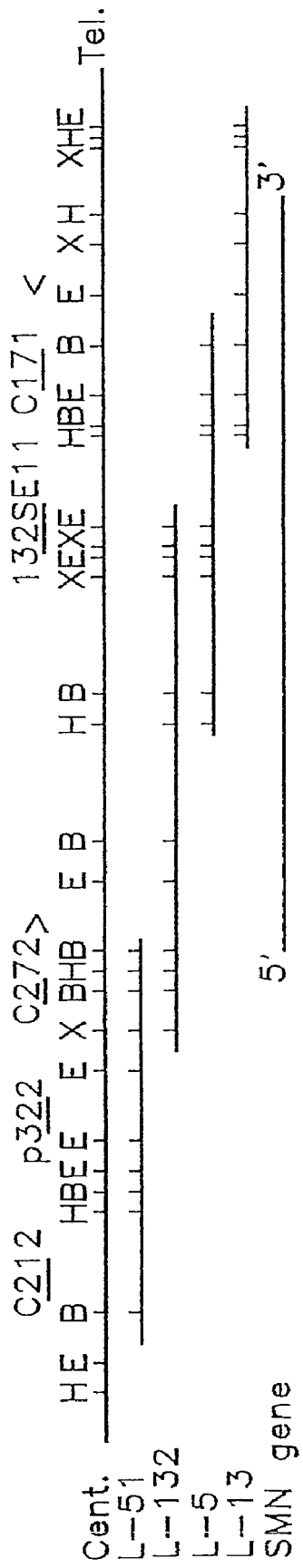

FIG.6

Telomeric element ($E^{Tel}$) containing the survival motor-neuron gene (SMN gene). Genetic map shows polymorphic markers C212, C272 and C171. Physical map shows location and direction of transcription of SMN gene; phage clones used for assembling physical map. Restriction map for EcoRI(E), XbaI(X), HindIII(H), BgIII(B), SacII(S) are shown. Cent. and Tel. indicate centromere and telomere respectively. The position of genomic rearrangements found in SMA patients are also indicated.

GENE DOSAGE ANALYSIS OF THE 5q13 REGION WITH THE 132SE11 PLASMID CONE IN SMA TYPE I PATIENT. TOTAL HUMAN DNA FROM SMA FAMILY WAS DIGESTED WITH HindIII FOR SOUTHERN BLOTTING. FILTER WAS CONSECUTIVELY HYBRIDIZED WITH 132SE11 (A) AND JK53 PROBES (B). A SIGNIFICANT DECREASE IN 132SE11 BAND INTENSITY, WHICH INDICATED THE DELETION, COMPARED WITH THEIR PARENTS. F/FATHER, M/MOTHER, A/AFFECTED

Figure 8

MAMSSGGSGGGVPEQEDSVLFRRGTGQSDDSDIWDDTALIKAYDKAVASFKHALKNG
DICETSGKPKTTPKRKPAKKNKSQKKNTAASLQQWKVGDKCSAIWSEDGCIYPATIA
SIDFKRETCVVVYTGYGNREEQNLSDLLSPICEVANNIEQNAQENENESQVSTDESE
NSRSPGNKSDNIKPKSAPWNSFLPPPPPMPGPRLGPGKPGLKFNGPPPPPPPPPHL
LSCWLPPFPSGPPIIPPPPPICPDSLDDADALGSMLISWYMSGYHTGYYM

Figure 10A 1
cctcccgggcaccgtactgttccgctcccagaagccccgggcgccggaagtcgtcac
tcttaagaagggacggggccccacgctgcgcacccgcgggtttgct ATG GCG
                                              M   A
ATG AGC AGC GGC GGC AGT GGT GGC GGC GTC CCG GAG CAG GAG
 M   S   S   G   G   S   G   G   G   V   P   E   Q   E
GAT TCC GTG CTG TTC CGG CGC GGC ACA GGC CAG gtgaggtcgcagc
 D   S   V   L   F   R   R   G   T   G   Q
cagtgcagtctcccattagcgctctcagcaccttcttccggcccaactctccttc
cgca
2a
gtgtaattttgttatgtgtggattaagatgactcttggtactaacatacatttctg
attaaacctatctgnacatgagttgttttatttcttacccttttccag AGC GAT
                                                  S   D
GAT TCT GAC ATT TGG GAT GAT ACA GCA CTG ATA AAA GCA TAT
 D   S   D   I   W   D   D   T   A   L   I   K   A   Y
GAT AAA GCT GTG GCT TCA TTT AAG gtatgaaatgcttgnttagtcgttt
 D   K   A   V   A   S   F   K
tcttattttctcgttattcatttggaaaggaattgataacatacgataaagtgttaa
2b
aggtgctttctgaggtgacggagccttgagactagcttatagtagtaactgggttat
gtcgtgacttttattctgtgcaccaccctgtaacatgtacattttattcctatttt
cgtag CAT GCT CTA AAG AAT GGT GAC ATT TGT GAA ACT TCG GGT
       H   A   L   K   N   G   D   I   C   E   T   S   G
AAA CCA AAA ACC ACA CCT AAA AGA AAA CCT GCT AAG AAG AAT
 K   P   K   T   T   P   K   R   K   P   A   K   K   N
AAA AGC CAA AAG AAG AAT ACT GCA GCT TCC TTA CAA CAG gttat
 K   S   Q   K   K   N   T   A   A   S   L   Q   Q
tttaaaatgttgaggatttaacttcaaaggatgtctcattagtccttatttaatagt
gtaaaatgtctttaact
3
gcctgcaggtcgatcaaaacgagatgatagtttgccctcttcaaaagaaatgtgtgc
atgtatatctttgatttcttttgtag TGG AAA GTT GGG GAC AAA TGT
                            W   K   V   G   D   K   C
TCT GCC ATT TGG TCA GAA GAC GGT TGC ATT TAC CCA GCT ACC
 S   A   I   W   S   E   D   G   C   I   Y   P   A   T
ATT GCT TCA ATT GAT TTT AAG AGA GAA ACC TGT GTT GTG GTT
 I   A   S   I   D   F   K   R   E   T   C   V   V   V
TAC ACT GGA TAT GGA AAT AGA GAG GAG CAA AAT CTG TCC GAT
 Y   T   G   Y   G   N   R   E   E   Q   N   L   S   D
CTA CTT TCC CCA ATC TGT GAA GTA GCT AAT AAT ATA GAA CAG
 L   L   S   P   I   C   E   V   A   N   N   I   E   Q

Figure 10B

```
AAT GCT CAA GAG gtaaggatacaaaaaaaaaaaaattcaatttctggaagcag
 N   A   Q   E
agactagatgagaaactgttaaacagtatacaca
4
ccaccgaggcattaattttttcttaatcacacccttataacaaaaacctgcatattt
tttcttttaaag AAT GAA AAT GAA AGC CAA GTT TCA ACA GAT GAA
              N   E   N   E   S   Q   V   S   T   D   E
AGT GAG AAC TCC AGG TCT CCT GGA AAT AAA TCA GAT AAC ATC
 S   E   N   S   R   S   P   G   N   K   S   D   N   I
AAG CCC AAA TCT GCT CCA TGG AAC TCT TTT CTC CCT CCA CCA
 K   P   K   S   A   P   W   N   S   F   L   P   P   P
CCC CCC ATG CCA GGG CCA AGA CTG GGA CCA GGA AAG gtaaacctt
 P   P   M   P   G   P   R   L   G   P   G   K
ctatgaaagttttccagaaaatagttaatgtcgggacatttaacctctctgttaact
aatttgtagctctccca
5
caaatattctgggtaattattttttatccttttggttttgagtcctttttattcctat
catattgaaattggtaagttaattttcctttgaaatattccttatag CCA GGT
                                                 P   G
CTA AAA TTC AAT GGC CCA CCA CCG CCA CCG CCA CCA CCA CCA
 L   K   F   N   G   P   P   P   P   P   P   P   P   P
CCC CAC TTA CTA TCA TGC TGG CTG CCT CCA TTT CCT TCT GGA
 P   H   L   L   S   C   W   L   P   P   F   P   S   G
CCA CCA gtaagtaaaaaagagtataggttagattttgctttcacatacaatttga
 P   P
taatta
6
ccagactttacttttgtttactggatataaacaatatcttttctgtctccag
ATA ATT CCC CCA CCA CCT CCC ATA TGT CCA GAT TCT CTT GAT
 I   I   P   P   P   P   P   I   C   P   D   S   L   D
GAT GCT GAT GCT TTG GGA AGT ATG TTA ATT TCA TGG TAC ATG
 D   A   D   A   L   G   S   M   L   I   S   W   Y   M
AGT GGC TAT CAT ACT GGC TAT TAT ATG gtaagtaatcactcagcatct
 S   G   Y   H   T   G   Y   Y   M
tttcctgacaattttttgtagttatgtgactttgtttggtaaatttataaaatact
acttg
7
aactgcagcctaataattgttttctttgggataacttttaaagtacattaaaagact
atcaacttaatttctgatcatatttgttgaataaaataagtaaaatgtcttgtgaa
```

Figure 10C

```
                                                              → a
acaaaatgcttttaacatccatataaagctatctatatatagctatctatgtctat
                                          → T
atagctattttttttaacttccttttattttccttacag GGT TTC AGA CAA
                                        G   F   R   Q
AAT CAA AAA GAA GGA AGG TGC TCA CAT TCC TTA AAT taaggagta
 N   Q   K   E   G   R   C   S   H   S   L   N  *
aagtctgccagcattatgaaagtgaatcttactttgtaaaactttatggtttgtgg
                                        → g
aaaacaaatgttttgaacagttaaaagttcagatgttaaaaagttgaaggttaa
tgtaaaacaatcaatattaaagaattttgatgccaaaactattagataaaaggttaa
                                        → g
tctacatccctactagaattctcatacttaactggttggttatgtggaagaaacata
ctttcacaataaagagctttaggatatgatgccatttttatatcactagtaggcagac
cagcagacttttttttattgtgatatgggataacctaggcatactgcactgtacact
ctgacatatgaagtgctctagtcaagtttaactggtgtccacagaggacatggttta
                                        8
actggaattcgtcaagcctctggttctaatttctcatttgcaggaaatgctggcata
gagcagcactaaatgacaccactaaagaaacgatcagacagatctggaatgtgaagc
gttatagaagataactggcctcatttcttcaaaatatcaagtgttgggaagaaaaa
aggaagtggaatgggtaactcttcttgattaaagttatgtaataaccaaatgcaat
                                        → a
gtgaaatattttactggactcttttgaaaaaccatctagtaaaagactggggtggg
gtgggaggccagcacggtggtgaggcagttgagaaatttgaatgtggattagattt
tgaatgatattggataattattggtaattttatggcctgtgagaagggtgttgtagt
ttataaaagactgtcttaatttgcatacttaagcatttaggaatgaagtgttagagt
gtcttaaaatgtttcaaatggtttaacaaaatgtatgtgaggcgtatgtggcaaaat
gttacagaatctaactggtggacatggctgttcattgtactgttttttctatcttc
tatatgtttaaaagtatataataaaaatattta
```

Figure 11

```
gatctgccttccttcctgccccatgtttgtctttccttgtttgtcttta       50 tatagatcaagcaggtttaaattcctagtaggagcttacatttactttt       100 ccaagggggagggggaataaatatctacacacacacacacacacacca        150
    H4TF-1       GH
cactggagttcgagacgaggcctaagcaacatgccgaaacccgtctcta       200
                          DTF-1
ctaaatacaaaaaatagctgagcttggtggcgcacgcctatagtcctagc      250 tactggggaggctgaggtgggaggatcgcttgagcccaagaagtcgaggc      300
         Sp1
tgcagtgagccgagatcgcgccgctgcactccagcctgagcgacagggcg      350 aggctctgtctcaaaacaaacaaacaaaaaaaaaaggaaaggaaatata       400
                                β-IFN
acacagtgaaatgaaaggattgagagaaatgaaaaatatacacgccacaa      450
                      HiNF-A
atgtgggagggcgataaccactcgtagaaagcgtgagaagttactacaag      500 cggtcctcccgggcaccgtactgttccgctcccagaagccccgggcgccg      550
                                    AP-2
gaagtcgtcactcttaagaagggacggggccccacgctgcgcacccgcgg      600
    E4F1
gtttgct ATG GCG ATG AGC AGC GGC GGC AGT GGT GGC          637
        M   A   M   S   S   G   G   S   G   G
```

Figure 12A

| | | | | | | | | | | | | |
|---|---|---|---|---|---|---|---|---|---|---|---|---|
| cggcgtggtagcaggcc | ATG | GCG | ATG | GGC | AGT | GGC | GGA | GCG | | | | 41 |
| | Met | Ala | Met | Gly | Ser | Gly | Gly | Ala | | | | |

```
GGC TCC GAG CAG GAA GAT ACG GTG CTG TTC CGG CGT GGC      80
Gly Ser Glu Gln Glu Asp Thr Val Leu Phe Arg Arg Gly

ACC GGC CAG AGT GAT GAT TCT GAC ATT TGG GAT GAT ACA     119
Thr Gly Gln Ser Asp Asp Ser Asp Ile Trp Asp Asp Thr

GCA TTG ATA AAA GCT TAT GAT AAA GCT GTG GCT TCC TTT     158
Ala Leu Ile Lys Ala Tyr Asp Lys Ala Val Ala Ser Phe

AAG CAT GCT CTA AAG AAC GGT GAC ATT TGT GAA ACT CCA     197
Lys His Ala Leu Lys Asn Gly Asp Ile Cys Glu Thr Pro

GAT AAG CCA AAA GGC ACA GCC AGA AGA AAA CCT GCC AAG     236
Asp Lys Pro Lys Gly Thr Ala Arg Arg Lys Pro Ala Lys

AAG AAT AAA AGC CAA AAG AAG AAT GCC ACA ACT CCC TTG     275
Lys Asn Lys Ser Gln Lys Lys Asn Ala Thr Thr Pro Leu

AAA CAG TGG AAA GTT GGT GAC AAG TGT TCT GCT GTT TGG     314
Lys Gln Trp Lys Val Gly Asp Lys Cys Ser Ala Val Trp

TCA GAA GAC GGC TGC ATT TAC CCA GCT ACT ATT ACG TCC     353
Ser Glu Asp Gly Cys Ile Tyr Pro Ala Thr Ile Thr Ser

ATT GAC TTT AAG AGA GAA ACC TGT GTC GTG GTT TAT ACT     392
Ile Asp Phe Lys Arg Glu Thr Cys Val Val Val Tyr Thr

GGA TAT GGA AAC AGA GAG GAG CAA AAC TTA TCT GAC CTA     431
Gly Tyr Gly Asn Arg Glu Glu Gln Asn Leu Ser Asp Leu

CTT TCC CCG ACC TGT GAA GTA GCT AAT AGT ACA GAA CAG     470
Leu Ser Pro Thr Cys Glu Val Ala Asn Ser Thr Glu Gln

AAC ACT CAG GAG AAT GAA AGT CAA GTT TCC ACA GAC GAC     509
Asn Thr Gln Glu Asn Glu Ser Gln Val Ser Thr Asp Asp

AGT GAA CAC TCC TCC AGA TCG CTC AGA AGT AAA GCA CAC     548
Ser Glu His Ser Ser Arg Ser Leu Arg Ser Lys Ala His
```

Figure 12B

```
AGC AAG TCC AAA GCT GCT CCG TGG ACC TCA TTT CTT CCT    587
Ser Lys Ser Lys Ala Ala Pro Trp Thr Ser Phe Leu Pro

CCA CCA CCC CCA ATG CCA GGG TCA GGA TTA GGA CCA GGA    626
Pro Pro Pro Pro Met Pro Gly Ser Gly Leu Gly Pro Gly

AAG CCA GGT CTA AAA TTC AAC GGC CCG CCG CCG CCG CCT    665
Lys Pro Gly Leu Lys Phe Asn Gly Pro Pro Pro Pro Pro

CCA CTA CCC CCT CCC CCC TTC CTG CCG TGC TGG ATG CCC    704
Pro Leu Pro Pro Pro Pro Phe Leu Pro Cys Trp Met Pro

CCG TTC CCT TCA GGA CCA CCA ATA ATC CCG CCA CCC CCT    743
Pro Phe Pro Ser Gly Pro Pro Ile Ile Pro Pro Pro Pro

CCC ATC TCT CCC GAC TGT CTG GAT GAC ACT GAT GCC CTG    782
Pro Ile Ser Pro Asp Cys Leu Asp Asp Thr Asp Ala Leu

GGC AGT ATG CTA ATC TCT TGG TAC ATG AGT GGC TAC CAC    821
Gly Ser Met Leu Ile Ser Trp Tyr Met Ser Gly Tyr His

ACT GGC TAC TAT ATG GGT TTC AGA CAA AAT AAA AAA GAA    860
Thr Gly Tyr Tyr Met Gly Phe Arg Gln Asn Lys Lys Glu

GGA AAG TGC TCA CAT ACA AAT taag                       885
Gly Lys Cys Ser His Thr Asn  *
```

Figure 13

```
      20         30         40         50         60         70
GSGGGVPEQEDSVLFRRGTGQSDDSDIWDDTALIKAYDKAVASFKHALKNGDICETS
====    ====-======================================= =====
GSGGAGSEQEDTVLFRRGTGQSDDSDIWDDTALIKAYDKAVASFKHALKNGDICETP
          20         30         40         50         60

80         90        100        110        120        130
GKPKTTPKRKPAKKNKSQKKNTAASLQQWKVGDKCSAIWSEDGCIYPATIASIDFKR
===-=  -==============---  = ==========-==============-======
DKPKGTARRKPAKKNKSQKKNATTPLKQWKVGDKCSAVWSEDGCIYPATITSIDFKR
   70         80         90        100        110        120

140        150        160        170        180         1
ETCVVVYTGYGNREEQNLSDLLSPICEVANNIEQNAQENENESQVSTDESENSRSPG
==========================  =====   ===--====--=======-== =
ETCVVVYTGYGNREEQNLSDLLSPTCEVANSTEQNTQENE--SQVSTDDSEHSSRSL
        130        140                160        170         1

90         200        210        220        230        240
NKSDNIKPKSAPWNSFLPPPPPMPGPRLGPGKPGLKFNGPPPPPPPPPHLLSCWLP
  =  =-====  ============   ===================  ===  = ===-=
RSKAHSKSKAAPWTSFLPPPPPMPGSGLGPGKPGLKFNGPPPPPPLPPPPFLPCWMP
80         190        200        210        220        230

250        260        270        280        290        300
PFPSGPPIIPPPPPICPDSLDDADALGSMLISWYMSGYHTGYYMGFRQNQKEGRCSH
==========================  ===-=====================  ====-===
PFPSGPPIIPPPPPISPDCLDDTDALGSMLISWYMSGYHTGYYMGFRQNKKEGKCSH
       240        250        260        270        280        290
```

SL
—
TN

SSCP ANALYSIS

▼ SMN
▽ C-BCD541

121B8 YAC

595CII YAC

HUMAN 1 CONTROL

HUMAN 2 CONTROL

HUMAN 3 CONTROL

HUMAN 4 SMA

SURVIVAL MOTOR NEURONS (SMN) GENE: A GENE FOR SPINAL MUSCULAR ATROPHY

This application is a Divisional of application Ser. No. 11/603,305 filed on Nov. 22, 2006, which is a Divisional of application Ser. No. 11/222,810 filed on Sep. 12, 2005 now abandoned, which is a Divisional of application Ser. No. 09/109,082, issued as U.S. Pat. No. 7,033,752, filed on Jul. 2, 1998, which is a Divisional of application Ser. No. 08/545,196, issued as U.S. Pat. No. 6,080,577, filed on Oct. 19, 1995, and for which priority is claimed under 35 U.S.C. §120; and this application claims priority of Application No. EP 94 402 353.0 filed in the European Patent Office on Oct. 19, 1994 under 35 U.S.C. §119; the entire contents of all are hereby incorporated by reference.

BACKGROUND OF THE INVENTION

1. Field of the Invention

The present invention relates to the discovery of the human survival motor-neuron gene or SMN gene which is a chromosome 5-SMA (Spinal Muscular Atrophy) determining gene. The present invention further relates to the nucleotide sequence encoding the SMN gene and corresponding amino acid sequence, a vector containing the gene encoding the SMN protein or a DNA sequence corresponding to the gene and transformant strains containing the SMN gene or a DNA sequence corresponding to the gene.

More particularly, the present invention relates to means and methods for detecting motor neuron diseases having symptoms of muscular weakness with or without sensory changes such as amytrophic lateral sclerosis (ALS), spinal muscular atrophy (SMA), primary lateral sclerosis (PLS), arthrogryposis multiplex congenita (AMC), and the like. The methods for detecting such motor neuron diseases include, but are not limited to, the use of specific DNA primers in the PCR technique, the use of hybridization probes and the use of polyclonal and monoclonal antibodies.

Even more particularly, the present invention relates to the use of the human SMN gene or part of the gene, cDNA, oligonucleotide or the encoded protein or part thereof in therapy by insertion of the human SMN gene or part of the gene, cDNA, oligonucleotide or the encoded protein or part thereof, if required, into engineered viruses or vectors that serve as harmless carriers to transport the gene or part of the gene, cDNA, oligonucleotide or the encoded protein or part thereof to the body's cells including bone marrow cells.

The invention further relates to antigen sequences directed to the SMN gene.

In order to provide means for the therapy of motor neuron diseases, the invention also relates to the protein encoded by the SMN gene.

The present invention also relates to the isolation of the mouse SMN gene, the nucleotide sequence encoding the mouse SMN gene and corresponding amino acid sequence. A transgenic mouse model that hyperexpresses all or part of the SMN gene and a transgenic mouse model produced by homologous recombination with a mutated SMN gene is also described.

2. State of the Art

Degenerative motor neuron diseases can be placed into three major categories. Amyotrophic lateral sclerosis or ALS, motor neuron diseases such as spinal muscular atrophy (SMA) and motor neuron diseases associated with other degenerative disorders such as primary lateral sclerosis (PLS).

Amyotrophic lateral sclerosis (ALS) is the most frequently encountered form of progressive neuron disease and is characteristically a disorder of middle age. The disease is characterized by progressive loss of motor neurons, both in the cerebral cortex and in the anterior horns of the spinal cord, together with their homologues in some motor nuclei of the brainstem. It typically affects both upper and lower motor neurons, although variants may predominantly involve only particularly subsets of motor neurons, particularly early in the course of illness.

ALS is evidenced by the development of asymmetric weakness, with fatigue and cramping of affected muscles. The weakness is accompanied by visible wasting and atrophy of the muscles evolves and over time, more and more muscles become involved until the disorder takes on a symmetric distribution in all regions, including muscles of chewing, swallowing and movement of the face and tongue. Fifty percent of patients having ALS can be expected to die within three to five years from the onset of the disease. Presently, there is no treatment that has influence on the pathologic process of ALS.

Spinal muscular atrophies (SMA) are characterized by degeneration of anterior horn cells of the spinal cord leading to progressive symmetrical limb and trunk paralysis associated with muscular atrophy. SMA represents the second most common fatal, autosomal recessive disorder after cystic fibrosis (1 out 6000 newborns). Childhood SMA is classically subdivided into three clinical groups on the basis of age of onset and clinical course. The acute form of Werdnig-Hoffmann disease (Type I) is characterized by severe generalized muscle weakness and hypotonia at birth or in the 3 months following birth. Death, from respiratory failure, usually occurs within the first two years. This disease may be distinguished from the intermediate (Type II) and juvenile (Type III, Kugelberg-Welander disease) forms. Type II children were able to sit but unable to stand or walk unaided, and they live beyond 4 years. Type III patients had proximal muscle weakness, starting after the age of two. The underlying biochemical defect remains unknown. In addition there is known to exist a slowly evolving adult form of SMA, sometimes referred to as SMA IV.

Primary lateral slcerosis (PLS) is a variant of ALS and occurs as a sporadic disease of late life. Neuropathologically in PLS there is a degeneration of the corticospinal (pyramidal) tracts, which appear almost normal at brainstem levels but become increasingly atrophic as they descend through the spinal column. The lower limbs are affected earliest and most severely.

Arthrogryposis Multiplex Congenita (AMC) is a frequent syndrome characterized by congenital joint fixation (incidence of 1 out of 3000 live births) resulting from decreased fetal movements in utero (Stern, W. G., JAMA, 81:1507-1510 (1923); Hall, J. G., *Clin. Orthop,* 194:44-53 (1985)). AMC has been ascribed to either oligo-hydramnios or a variety of diseases involving the central nervous system, skeletal muscle, or spinal cord. Since neuronal degeneration and neuronophagia occur in the anterior horns, it has been hypothesized that the AMC of neurogenic origin could be related to acute spinal muscular atrophy; SMA Type I Werdnig-Hoffman disease (Banker, B. Q., Hum. Pathol., (1986); 117:656-672).

The detection and clinical diagnosis for ALS, AMC, SMA and PLS is quite limited to muscle biopsies, the clinical diagnosis by a physician and electromyography (EMG). For example, the clinical criteria for diagnosing SMA is set forth in the Clinical Criteria International SMA Consortium (Munsat T. L, *Neuromuscular Disorders,* Vol. 1, p. 81 (1991)). But due to the complications of the various tests to detect motor neuron disorders, the clinician usually attempts to eliminate various categories of other disease states such as structural lesions, infections, intoxications, metabolic disorders and hereditary biochemical disorders prior to utilizing the above-described test methods.

Presently there is no treatment for any of the above-mentioned motor neuron disorders. Basic rehabilitative measures, including mechanical aids of various kinds, may help patients that have these diseases overcome the effects of their disabilities, but often confining respiratory support systems are necessary to have the patient survive longer.

Accordingly, it is an object of the present invention to characterize the SMA gene which is responsible for SMA disorders and to clone the SMA gene into a vector, for example a plasmid, a cosmid, a phage, a YAC vector, that can be used in the transformation process to produce large quantities of the SMN gene and SMN protein.

In yet another aspect of the invention is the use of primers and hybridization probes to detect and diagnose patients having motor neuron disorders such as AMC, ALS, SMA and PLS. Yet another aspect of the present invention is the use of the SMN gene or part thereof or cDNA, oligonucleotides, protein or part thereof in therapy to correct disorders present in, for example AMC, SMA, ALS and PLS patients, especially gene disorders.

In yet another aspect, the present invention provides monoclonal and polyclonal antibodies for detection of SMN gene defects in SMA patients.

Another object of the present invention provides the characterization of the SMA gene in the mouse. A transgenic mouse model is presented that hyperexpresses all or part of the SMN gene or a transgenic mouse that by homologous recombination with a mutated mouse SMN gene produces abnormalities in the SMN gene is also described.

According to a further aspect of the invention, the therapy of motor neuron diseases can involve the protein encoded by the SMN gene.

These and other objects are achieved by the present invention as evidenced by the summary of the invention, the description of the preferred embodiments and the claims.

OBJECTS AND SUMMARY OF THE INVENTION

It is an object of the present invention to provide a novel human Survival Motor Neuron gene or SMN gene, its DNA sequence and amino acid sequence.

Another aspect of the present invention provides a novel mouse Survival Motor Neuron gene or SMN gene, its DNA sequence and amino acid sequence.

Yet another aspect of the present invention is the provision of a vector which is capable of replicating in a host microorganism to provide large quantities of the human or mouse SMN protein.

Yet another aspect of the present invention is the provision of specific DNA sequences that can be used to detect and diagnose spinal muscular atrophy and other motor neuron disorders. These DNA sequences can be used as primers in the polymerase chain reaction to amplify and detect the SMN gene sequence, a truncated or mutated version of the SMN gene sequence or lack of said sequence which leads to the diagnosis of SMA, AMC, and other motor neuron disorders.

Yet another aspect of the present invention provides a transgenic mouse that hyperexpresses all or part of the SMN gene or a transgenic mouse that by homologous recombination with a mutated mouse SMN gene produces abnormalities in the SMN gene is also described.

The inventors have identified two genes respectively designated TBCD541 and C-BCD541, which are involved in motor neuron disorders.

The T-BCD541 gene is responsible for the motor neuron diseases of the SMA type, since its alteration either by partial or total deletion, by mutation or any other modification, is sufficient to lead to a pathological state at the clinical electromyographic or muscle morphological levels.

The C-BCD541 gene is different from the T-BCD541 gene, at the level of the cDNA, since two nucleotides are modified. This C-BCD541 gene is nevertheless not correctly processed during the transcription in controls and patients suffering from motor neuron diseases. The genomic DNA of the C-BCD541 gene is not correctly spliced during the transcription providing thus for an abnormal transcript. The difference between the splicing of the T-BCD541 and the C-BCD541 gene results from differences in the sequence of the introns of these genes.

The present invention thus further characterizes the structure and organization of the human SMN gene which was found to be approximately 20 kb in length and consists of 9 exons interrupted by 8 introns. The nucleotide sequence, amino acid sequence as well as the exon-intron boundaries of the human SMN gene is set forth in FIG. 10. All exon-intron boundaries display the consensus sequence found in other human genes. A polyadenylation consensus site is localized about 550 bp downstream from the stop colon (FIG. 10). The entire intron/exon structure of the SMN gene permits the characterizations of the SMN gene mutations in SMA disease or other motor neuron diseases.

The present invention also defines means for the detection of genomic abnormalities relating to motor neuron diseases at the level of the T-BCD541 gene or at the level of the C-BCD541 gene.

The genes of the invention can be further defined in that each of them comprise intronic sequences corresponding to the following sequences:

```
In the T-BCD541 gene
for intron n° 6:
                                      (SEQ ID NO: 1)
5'AATTTTTAAATTTTTTGTAGAGACAGGGTCTCATTATGTTGCCCA
GGGTGGTGTCAAGCTCCAGGTCTCAAGTGATCCCCCTACCTCCGCCT
CCCAAAGTTGTGGGATTGTAGGCATGAGCCACTGCAAGAAAACCTTA
ACTGCAGCCTAATAATTGTTTTCTTTGGGATAACTTTTAAAGTACAT
TAAAAGACTATCAACTTAATTTCTGATCATATTTTGTTGAATAAAAT
AAGTAAAATGTCTTGTGAACAAAATGCTTTTTAACATCCATATAAAG
CTATCTATATATAGCTATCTATGTCTATATAGCTATTTTTTTTAACT
TCCTTTTATTTTCCTTACAG 3' for intron n° 7:
                                      (SEQ ID NO: 2)
5'GTAAGTCTGCCAGATTATGAAAGTGAATCTTACTTTTGTAAAACT
TTATGGTTTGTGGAAAACAAATGTTTTTGAACAGTTAAAAAGTTCAG
ATGTTAAAAAGTTGAAAGGTTAATGTAAAACAATCAATATTAAAGAA
TTTTGATGCCAAAACTATTAGATAAAAGGTTAATCTACATCCCTACT
AGAATTCTCATACTTAACTGGTTGGTTATGTGGAAGAAACATACTTT
CACAATAAAGAGCTTTAGGATATGATGCCATTTTATATCACTAGTAG
GCAGACCAGCAGACTTTTTTTTATTGTGATATGGGATAACCTAGGCA
TACTGCACTGTACACTCTGACATATGAAGTGCTCTAGTCAAGTTTAA
CTGGTGTCCACAGAGGACATGGTTTAACTGGAATTCGTCAAGCCTCT
GGTTCTAATTTCTCATTTGCAG 3'

In the C-BCD541 gene:
for intron n° 6:
                                      (SEQ ID NO: 3)
5'AATTTTTAAATTTTTTGTAGAGACAGGGTCTCATTATGTTGCCCA
GGGTGGTGTCAAGCTCCAGGTCTCAAGTGATCCCCCTACCTCCGCCT
CCCAAAGTTGTGGGATTGTAGGCATGAGCCACTGCAAGAAAACCTTA
```

```
-continued
ACTGCAGCCTAATAATTGTTTTCTTTGGGATAACTTTTAAAGTACAT
TAAAAGACTATCAACTTAATTTCTGATCATATTTTGTTGAATAAAAT
AAGTAAAATGTCTTGTGAACAAAATGCTTTTTAACATCCATATAAAG
CTATCTATATATAGCTATCTATATCTATATAGCTATTTTTTTTAACT
TCCTTTTATTTTCCTTACAG* for intron nº 7:
                                      (SEQ ID NO: 4)
*GTAAGTCTGCCAGCATTATGAAAGTGAATCTTACTTTTGTAAAACT
TTATGGTTTGTGGAAAACAAATGTTTTTGAACAGTTAAAAAGTTCAG
ATGTTAGAAAGTTGAAAGGTTAATGTAAAACAATCAATATTAAAGAA
TTTTGATGCCAAAACTATTAGATAAAAGGTTAATCTACATCCCTACT
AGAATTCTCATACTTAACTGGTTGGTTGTGTGGAAGAAACATACTTT
CACAATAAAGAGCTTTAGGATATGATGCCATTTTATATCACTAGTAG
GCAGACCAGCAGACTTTTTTTATTGTGATATGGGATAACCTAGGCA
TACTGCACTGTACACTCTGACATATGAAGTGCTCTAGTCAAGTTTAA
CTGGTGTCCACAGAGGACATGGTTTAACTGGAATTCGTCAAGCCTCT
GGTTCTAATTTCTCATTTGCAG*
```

In a preferred embodiment of the invention, the gene of the invention is capable of hybridizing in stringent conditions with the sequence of FIG. 3 (SEQ ID NOS: 12-13) used as probe.

As hereabove written, the invention further relates to a variant of the SMN gene, which variant is a C-BCD541 gene having a cDNA sequence corresponding to the sequence of FIG. 2 (SEQ ID NOS: 10-11).

The invention also relates to cDNA sequences such as obtained from one of the above genes. Such cDNA sequences are disclosed in FIGS. 2 and 3. Both of these cDNA sequence are capable of encoding a protein comprising the amino acid sequence described in FIG. 1 (SEQ ID NO: 9).

Despite this capacity to encode for such a protein, the inventors have noted that the C-BCD541 gene is able to produce in vivo this protein or is not able to produce it in a sufficient quantity due to the abnormal splicing of the gene during the transcription. Thus, the presence of the C-BCD541 gene does not enable to correct in vivo the deficiency (deletion, mutation, . . . ) of the T-BCD541 gene responsible for the motor neuron diseases of the SMA type or other motor neuron disorders.

In a particular embodiment, the invention relates also to a nucleotide sequence comprising nucleotides 34 to 915 of the sequence of FIG. 3, or to a sequence comprising nucleotides 34 to 915 of the sequence of FIG. 2.

These nucleotide sequences correspond to the coding sequence of respectively the T-BCD541 gene and C-BCD541 gene.

The introns of the hereabove described genes are also included in the application. Especially introns 6 and 7 have respectively the following sequences:

```
For the T-BCD541 gene:
Intron 6:
                                      (SEQ ID NO: 1)
5'AATTTTTAAATTTTTTGTAGAGACAGGGTCTCATTATGTTGCCCA
GGGTGGTGTCAAGCTCCAGGTCTCAAGTGATCCCCCTACCTCCGCCT
CCCAAAGTTGTGGGATTGTAGGCATGAGCCACTGCAAGAAAACCTTA
ACTGCAGCCTAATAATTGTTTTCTTTGGGATAACTTTTAAAGTACAT
TAAAAGACTATCAACTTAATTTCTGATCATATTTGTTGAATAAAAT
AAGTAAAATGTCTTGTGAACAAAATGCTTTTTAACATCCATATAAAG
CTATCTATATATAGCTATCTATGTCTATATAGCTATTTTTTTTAACT
TCCTTTTATTTTCCTTACAG 3'

Intron 7:
                                      (SEQ ID NO: 2)
5'GTAAGTCTGCCAGCATTATGAAAGTGAATCTTACTTTTGTAAAAC
TTTATGGTTTGTGGAAAACAAATGTTTTTGAACAGTTAAAAAGTTCA
GATGTTAAAAAGTTGAAAGGTTAATGTAAAACAATCAATATTAAAGA
ATTTTGATGCCAAAACTATTAGATAAAAGGTTAATCTACATCCCTAC
TAGAATTCTCATACTTAACTGGTTGGTTATGTGGAAGAAACATACTT
```

```
-continued
TCACAATAAAGAGCTTTAGGATATGATGCCATTTTATATCACTAGTA
GGCAGACCAGCAGACTTTTTTTATTGTGATATGGGATAACCTAGGC
ATACTGCACTGTACACTCTGACATATGAAGTGCTCTAGTCAAGTTTA
ACTGGTGTCCACAGAGGACATGGTTTAACTGGAATTCGTCAAGCCTC
TGGTTCTAATTTCTCATTTGCAG 3'

For the C-BCD541 gene:
Intron 6:
                                      (SEQ ID NO: 3)
5'AATTTTTAAATTTTTTGTAGAGACAGGGTCTCATTATGTTGCCCA
GGGTGGTGTCAAGCTCCAGGTCTCAAGTGATCCCCCTACCTCCGCCT
CCCAAAGTTGTGGGATTGTAGGCATGAGCCACTGCAAGAAAACCTTA
ACTGCAGCCTAATAATTGTTTTCTTTGGGATAACTTTTAAAGTACAT
TAAAAGACTATCAACTTAATTTCTGATCATATTTTGTTGAATAAAAT
AAGTAAAATGTCTTGTGAACAAAATGCTTTTTAACATCCATATAAAG
CTATCTATATATAGCTATCTATATCTATATAGCTATTTTTTTTAACT
TCCTTTTATTTTCCTTACAG*

Intron 7:
                                      (SEQ ID NO: 4)
GTAAGTCTGCCAGCATTATGAAAGTGAATCTTACTTTTGTAAAACTT
TATGGTTTGTGGAAAACAAATGTTTTTGAACAGTTAAAAAGTTCAGA
TGTTAGAAAGTTGAAAGGTTAATGTAAAACAATCAATATTAAAGAAT
TTTGATGCCAAAACTATTAGATAAAAGGTTAATCTACATCCCTACTA
GAATTCTCATACTTAACTGGTTGGTTGTGTGGAAGAAACATACTTTC
ACAATAAAGAGCTTTAGGATATGATGCCATTTTATATCACTAGTAGG
CAGACCAGCAGACTTTTTTTATTGTGATATGGGATAACCTAGGCAT
ACTGCACTGTACACTCTGACATATGAAGTGCTCTAGTCAAGTTTAAC
TGGTGTCCACAGAGGACATGGTTTAACTGGAATTCGTCAAGCCTCTG
GTTCTAATTTCTCATTTGCAG*
```

The invention further encompasses a nucleotide sequence, characterized in that it comprises at least around 9 nucleotides and in that it is comprised within a sequence which has been described above or in that it hybridizes with a sequence as described above in hybridization conditions which are determined after choosing the oligonucleotide.

For the determination of the hybridization conditions, reference is made to the hybridization techniques for oligonucleotides probes such as disclosed in Sambrook et al, Molecular Cloning, a Laboratory Manual, 2nd edition, 1989.

The sequences of the invention are either DNA (especially genomic DNA or cDNA or synthetic DNA) or RNA. They can be used as probes for the detection of the T-BCD541 or C-BCD541 genes or as primers for the amplification of genomic DNA present in a biological sample.

Preferred primers are those comprising or relating to the following sequences:

```
                                      (SEQ ID NO: 5)
   a) 5' AGACTATCAACTTAATTTCTGATCA 3'  (R 111)

(SEQ ID NO: 6)
   b) 5' TAAGGAATGTGAGCACCTTCCTTC 3'  (541C770)
```

The above primers are characteristic of exon 7 of the T-BCD541 gene.

```
                                      (SEQ ID NO: 7)
   (c)      GTAATAACCAAATGCAATGTGAA  (541C960)

(SEQ ID NO: 8)
   (d)      CTACAACACCCTTCTCACAG     (541C1120)
```

The above primers are characteristic of exon 8 of the T-BCD541 gene.

The primers used by pairs can form sets for the amplification of genomic DNA in order to detect motor neuron diseases.

Inverted complementary sequences with respect to the above primers can also be used.

Preferred sets of primers are the following:
a pair of primers contained in the sequence comprising nucleotides 921 to 1469 of the sequence of FIG. 3 and/or
a pair of primers comprising the following sequences:

5' AGACTATCAACTTAATTTCTGATCA 3'    (SEQ ID NO: 5)

5' TAAGGAATGTGAGCACCTTCCTTC 3'    (SEQ ID NO: 6)

Another preferred set of primers comprises:
a pair of primers having the following sequences:

5' AGACTATCAACTTAATTTCTGATCA 3'    (SEQ ID NO: 5)

5' TAAGGAATGTGAGCACCTTCCTTC 3'    (SEQ ID NO: 6)

a pair of primers having the following sequences:

5' GTAATAACCAAATGCAATGTGAA 3'    (SEQ ID NO: 7)
and/or

5' CTACAACACCCTTCTCACAG 3'    (SEQ ID NO: 8)

From a general point of view for the detection of divergence in exon 7, between the T-BCD541 and C-BCD541 genes oligonucleotide primers can be selected in the fragment 5' from the divergence and within exon 7 or intron 7.

Other primers that can be used for SSCP analysis for diagnostic purposes are selected from amongst the following:

```
5' EXON 1    121md/121me    Size: 170 bp
                                       (SEQ ID NO: 24)
121MD        5' AGG GCG AGG CTC TGT CTC A (SEQ ID NO: 25)
121ME        5' CGG GAG GAC CGC TTG TAG T EXON1        121ma/121mf    Size: 180 bp
                                       (SEQ ID NO: 26)
121MA        5' GCC GGA AGT CGT CAC TCT T (SEQ ID NO: 27)
121MF        5' GGG TGC TGA GAG CGC TAA TA EXON2A       Ex2A5/Ex2A3    Size: 242 bp
                                       (SEQ ID NO: 28)
EX2A5        5' TGT GTG GAT TAA GAT GAC TC (SEQ ID NO: 29)
EX2A3        5' CAC TTT ATC GTA TGT TAT C EXON2B       Ex2B5/EX23     Size: 215 bp
                                       (SEQ ID NO: 30)
EX2B5        5' CTG TGC ACC ACC CTG TAA CAT G (SEQ ID NO: 31)
EX23         5' AAG GAC TAA TGA GAC ATC C EXON3        SM8C/161CR2    Size: 238 bp
                                       (SEQ ID NO: 32)
SM8C         5' CGA GAT GAT AGT TTG CCC TC (SEQ ID NO: 33)
161CR2       5' AG CTA CTT CAC AGA TTG GGG AAA G SM8D/C260      Size: 150 bp
                                       (SEQ ID NO: 34)
SM8D         5' CTC ATC TAG TCT CTG CTT CC (SEQ ID NO: 35)
541C260      5' TGG ATA TGG AAA TAG AGA GGG AGC EXON4        SM3CA/C460     Size: 150 bp
                                       (SEQ ID NO: 36)
SM3CA        5' CAC CCT TAT AAC AAA AAC CTG C (SEQ ID NO: 37)
541C460      5' GAG AAA GGA GTT CCA TGG AGC AG SM3CB/C380     Size: 180 bp
                                       (SEQ ID NO: 38)
SM3CB        5' GAG AGG TTA AAT GTC CCG AC (SEQ ID NO: 39)
541C380      5' GTG AGA ACT CCA GGT CTC CTG G EXON5        EX55/C590      Size: 254 bp
                                       (SEQ ID NO: 40)
EX55         5' TGA GTC TGT TTG ACT TCA GG (SEQ ID NO: 41)
541C590      5' GAA GGA AAT GGA GGC AGC CAG C EX53/C550      Size: 168 bp
                                       (SEQ ID NO: 42)
EX53         5' TTT CTA CCC ATT AGA ATC TGG (SEQ ID NO: 43)
541C550      5' CCC CAC TTA CTA TCA TGC TGG CTG EXON6        164C25/C849    Size: 143 bp
                                       (SEQ ID NO: 44)
164C25       5' CCA GAC TTT ACT TTT TGT TTA CTG (SEQ ID NO: 45)
541C849      5' ATA GCC ACT CAT GTA CCA TGA EX63/C618      Size: 248 bp
                                       (SEQ ID NO: 46)
EX63         5' AAG AGT AAT TTA AGC CTC AGA CAG (SEQ ID NO: 47)
541C618      5' CTC CCA TAT GTC CAG ATT CTC TTG 3'

EXON7        R111/C770      Size: 200 bp
                                       (SEQ ID NO: 48)
R111         5' AGA CTA TCA ACT TAA TTT CTG ATC A (SEQ ID NO: 49)
541C770      5' TAA GGA ATG TGA GCA CCT TCC TTC R111/C261      Size: 244 bp
                                       (SEQ ID NO: 50)
R111         5' AGA CTA TCA ACT TAA TTT CTG ATC A (SEQ ID NO: 51)
164C261      5' GTA AGA TTC ACT TTC ATA ATG CTG INTRON7      164C45/164C265 Size: 220 bp
                                       (SEQ ID NO: 52)
164C45       5' CTT TAT GGT TTG TGG AAA ACA 3'

(SEQ ID NO: 53)
164C265      5' GGC ATC ATA TCC TAA AGC TC

EXON8        C960/C1120     Size: 186 bp
                                       (SEQ ID NO: 54)
541C960      5' GTA ATA ACC AAA TGC AAT GTG AA (SEQ ID NO: 55)
541C1120     5' CTA CAA CAC CCT TCT CAC AG 164C140/C920
                                       (SEQ ID NO: 56)
164C140      5' GGT GTC CAC AGA GGA CAT GG (SEQ ID NO: 57)
541C920      5' AAG AGT TAA CCC ATT CCA GCT TCC
```

The invention also concerns antisense DNA or RNA, capable of hybridizing with the C-BCD541 gene and particularly to the intron sequences, especially with the fragment of the introns which differ from the corresponding part in the T-BCD541 gene.

The invention also relates to a protein comprising the amino acid sequence of FIG. 1, or to a protein having the amino acid sequence of FIG. 8.

The protein relating to the sequence of FIG. 1 can be used in a composition for the treatment of motor neuron diseases, via oral, intra-muscular, intravenous administration, or via administration in the spinal cord fluid.

The invention further provides a kit for the in vitro diagnosis of motor neuron diseases, comprising
  a set of primers as described above;
  reagents for an amplification reaction; and
  a probe for the detection of the amplified product.

According to another embodiment of the invention, a kit for the detection of the motor neuron diseases containing a hybridization probe as described above is provided.

Oligonucleotide probes corresponding to the divergences between the genes can be used.

The diagnosis can be especially directed to SMA motor neuron pathology.

The invention also concerns cloning or expression vectors comprising a nucleotide sequence as defined above. Such vectors can be, for example, plasmids, cosmids, phages, YAC, pYAC, and the like. Preferably, such a vector has a motor neuron tropism. Especially for the purpose of defining means for gene therapy, it can be chosen among poliovirus vector, herpes virus, adenovirus, retrovirus vectors, synthetic vectors and the like.

Within the scope of the invention are contemplated further recombinant sequences. The invention also concerns recombinant host cells, i.e., yeasts, CHO cells, baculovirus, bone marrow cells, E. coli, fibroblasts-epithelial cells, transformed by the above recombinant sequences.

The invention also relates to a method for detecting motor neuron disorders including spinal muscular atrophy, amyotrophoc lateral sclerosis and primary lateral sclerosis, said method comprising the steps of:
  (a) extracting DNA from a patient sample;
  (b) amplifying said DNA with primers as described above;
  (c) subjecting said amplified DNA to SCCP;
  (d) autoradiographing the gels; and
  (e) detecting the presence or absence of the motor neuron disorder.

Steps (c) and (d) can be replaced by a step of digestion with Bsrt enzyme or with any other enzyme capable of recognizing specifically the divergence of the genes or mismatches in genes, or by sequencing.

The invention also relates to a method for detecting spinal muscular atrophy, said method comprising the steps of:
  (a) extracting DNA from a patient sample;
  (b) hybridizing said DNA with a DNA probe comprising all or part of the cDNA sequence of FIG. 3 or of FIG. 2 under stringent conditions; and
  (c) detecting the hybrids possible formed.

The invention also relates to a method for detecting arthrogryposis multiplex congenita, said method comprising the steps of:
  (a) extracting DNA from a patient sample;
  (b) amplifying said DNA via PCR using unlabeled primers from exon 7 and exon 8 of the SMN gene;
  (c) subjecting said amplified DNA to SCCP;
  (d) autoradiographing the gels; and
  (e) detecting the presence or absence of arthrogryposis multiplex congenita.

Yet another method to detect arthrogryposis multiplex congenita concerns dinucleotide Repeat Polymorphism Analysis using genotyping markers C272 and C212 after PCR amplification.

The present invention further concerns polyclonal antiserum or monoclonal antibodies directed to the protein of FIG. 1 (SEQ ID NO: 9), the protein of FIG. 8 (SEQ ID NO: 19) or the protein of FIG. 12 (SEQ ID NO: 20).

Yet another aspect of the present invention is directed to the use of the entire or partial nucleotide sequence of SMN as a probe to detect SMA as well as to identify and clone genes related to SMN gene motor neuron in animals or organisms.

Yet another aspect of the present invention is the use of the SMA protein to produce polyclonal and monoclonal antibodies, which antibodies may be used to detect and diagnose SMA.

In another aspect, polyclonal rabbit antiserum were generated against synthetic peptides corresponding to the amino acid sequence of FIGS. 1, 8 and 12, including the amino acid terminus and the carboxy terminus.

Accordingly, in one of its process aspects, the present invention relates to the detection of SMA in patients having SMA or related motor neuron disorders such as AMC, ALS and PLS.

Yet another aspect of the present invention is to administer the SMN gene part thereof, cDNA or oligonucleotides to patients who are either lacking the gene or have a genetically defective gene as such or after incorporation into engineered viruses or vectors.

These and other aspects of the present invention will be discussed in detail below in the preferred embodiments of the present invention.

BRIEF DESCRIPTION OF THE DRAWINGS

FIG. 1 (SEQ ID NO: 9) is the amino acid sequence of the SMN coding region of the clone T-BCD541.

FIG. 2A (SEQ ID NO: 10) is the nucleotide sequence of the SMN coding region as well as the 5' and 3' flanking regions of clone C-BCD541; the coding region is underlined.

FIG. 2B (SEQ ID NO: 11) contains the sequence starting from intron 6 up to exon 8 of the C-BCD541 gene. The underlined sequences are those of exons 7 and 8. Sequences of introns 6 and 7 can be chosen as oligonucleotides to amplify the cDNA region allowing the distinction, within exon 7, between the T-BCD541 gene and the C-BCD541 gene. The position of the divergent nucleotide between the T-BCD541 and C-BCD541 cDNA are in italics.

FIG. 3A (SEQ ID NO: 12) is the nucleotide sequence of the SMN coding region as well as the 5' and 3' flanking regions of clone T-BCD541. The coding sequences are underlined. The numbers of the exons are indicated on the sequence. Asteriks indicate the beginning of each exon. The nucleotides which are indicated in italics are those which differ between the C-BCD541 and the T-BCD541 genes.

FIG. 3B (SEQ ID NO: 13) represents the sequence from intron 6 up to the end of exon 8 of the T-BCD541 gene. The sequence of exons 7 and 8 is underlined.

FIG. 4 is the nucleotide sequences of the markers C212 (SEQ ID NO: 14), C272 (SEQ ID NO: 15), C171 (SEQ ID NO: 18), AFM157xd10 (SEQ ID NO: 16), and C161 (SEQ ID NO: 17).

FIG. 5 represents various probes utilized in the present invention revealing several loci that the probes hybridized to.

FIG. 6 represents the telomeric element containing the survival SMN gene.

FIG. 8 (SEQ ID NO: 19) represents the amino acid sequence of the truncated SMN protein.

FIG. 10 (SEQ ID NO: 22)represents the nucleotide sequence and amino acid sequence of the entire human SMN gene including the introns and exons. Translated nucleotide sequences are in upper case, with the corresponding amino acids shown below that. The polyadenylation signal is in bold face. Arrowheads indicate the position of the single base differences between SMN and C-BCD541 genes in introns 6 and 7 and exons 7 and 8. Italic letters indicate the position of the oligonucleotides chosen for the detection of divergences in intron 7. (*) indicates the position of the stop codon.

FIG. 11 (SEQ ID NO: 23) represents the nucleotide sequence upstream of the coding region of the human SMN gene and illustrates the presence of putative binding sites for the transcription factors of AP-2, GH-CSE2, DTF-1, E4F1, HINF-A, H4TF-1, β-IFN and SpI. Bold letters indicate the dinucleotide repeat (CA) corresponding to the C272 markers.

FIG. 12 (SEQ ID NO: 20) represents the nucleotide and amino acid sequences of Mouse SMN cDNA. (*) indicates the position of the stop codon.

FIG. 13 represents a comparative analysis of the amino acid sequence of human SMN (above) and mouse SMN (below).

DETAILED DESCRIPTION OF THE PREFERRED EMBODIMENTS OF THE INVENTION

Figure 5:
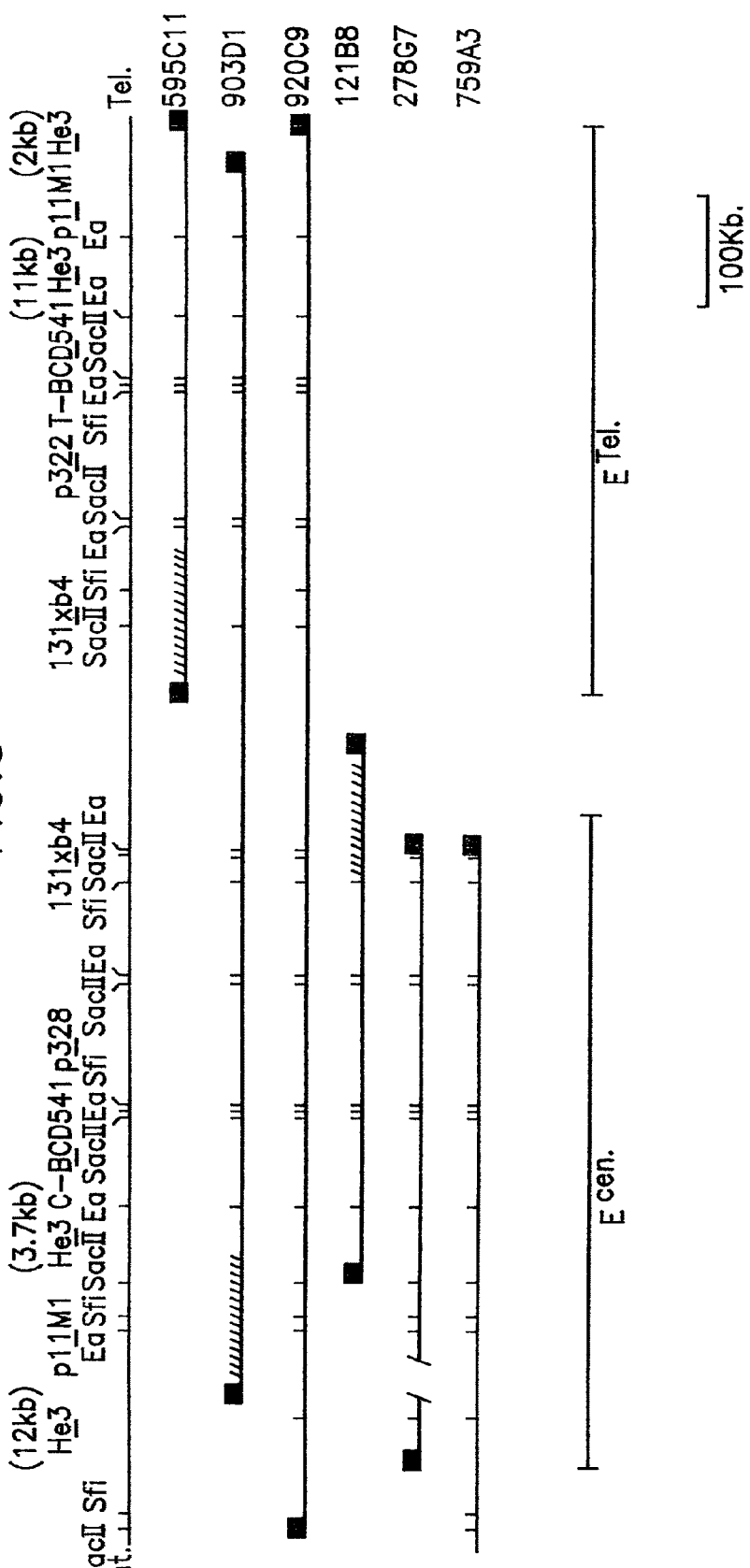
Figure 7:
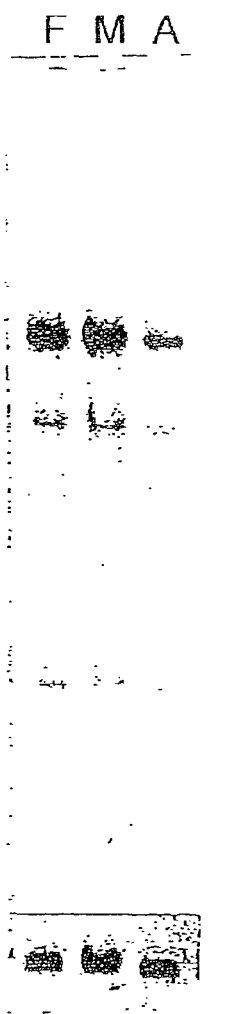
FIG. 7 represents the marked decrease of gene dosage with probe 132SEII, mapping close to this.

As used herein, the term "contig" means overlapping nucleotide sequences.

Previous studies by means of linkage analysis have shown that all three forms of spinal muscular atrophy map to chromosome 5q11.2-q13.3. (L M. Brzustowicz et al, *Nature,* 344, 5-10 (1990); J. Melki et al, *Nature,* 345, 823 (1990); J. Melki et al, *Lancet,* 336, 271 (1990). A yeast artificial chromosome (YAC) contig of the 5q13 region spanning the disease locus was constructed that showed the presence of low copy-repeats in this region. Allele segregation was analyzed at the closest genetic loci detected by markers derived from the YAC contig (C212, C272 and C161) in 201 SMA families. These markers revealed two loci (C212, C272) or three loci on the 5q13 region (C161). Inherited and de novo deletions were observed in 9 unrelated SMA patients. Moreover, deletions were strongly suggested in at least 18% of SMA type I patients by the observation of marked heterozygosity deficiency for the loci studied. These results indicated that deletion events are statistically associated with the severe form of SMA.

By studying all polymorphic DNA markers derived from the YAC contig, it was observed that the smallest rearrangement occurred within a region bordered by loci detected by C161 and C212-C272 and entirely contained in a 1.2-Mb YAC clone 903D1. See, for example, French Patent Application No. 9406856 incorporated herein by reference.

The present invention characterized the small nested critical SMA region of about 140 Kb by a combination of genetic and physical mapping in SMA patients. This region suggested a precise location for the SMA gene and therefore, a limited region within which to search for candidate genes. The present invention identified a duplicated gene from the 5q13 region. One of them (the telomeric gene) is localized within the critical region. Moreover, this gene was lacking in 213 out of 230 (92.2%) or interrupted in 13 out of 230 (5.6%) SMA patients. In patients where the telomeric gene is not lacking or interrupted, deleterious mutations indicated that this telomeric gene, termed survival motor-neuron (SMN) gene, is the chromosome 5 SMA-determining gene.

The SMN gene was discovered using a complex system of restriction mapping, distinguishing the $E^{Tel}$ from the $E^{Cen}$ by Southern blot, and the determination of the differences between the $E^{Tel}$ in SMA patients by genetic and physical mapping. After confirming the location of the SMN gene, a phage contig spanning the critical region of the telomeric element was constructed to identify specific clones containing the SWN gene.

Analysis of the SMN gene in SMA patients compared with those of normal patients revealed either the SMN gene was either lacking or truncated in 98% of SMA patients or had combined mutations not present in normal control patients.

To identify a large inverted duplication and a complex genomic organisation of the 5q13 region, long-range restriction mapping using pulsed field gel electrophoresis (PFGE) of the YAC contig was performed.

YACs were ordered by comparing their haplotypes with that of the human donor at the polymorphic loci detected markers C212, C272, C171 C161 (FIG. 4 (SEQ ID NOS: 14-18)).

The restriction enzymes SacII, BssHII, SfiI, EagI and XhoI were used to digest the YACs containing the telomeric loci detected by markers C212, C272, C171 and C161 (YAC clone 595C11), the centromeric loci detected by these markers (YAC clones 121B8, 759A3, 278G7) or both (YAC clones 903D1 and 920C9). Lambda phage libraries of YACs 595C11, 121B8 and 903D1 were constructed and subclones from phages containing markers C212 (p322), C272 (132SE11), C161(He3), AFM157xd10(131xb4) and CMS1 (p11M1) were used as probes for PFGE analysis. FIG. 5 shows that probes 132SE11, 11P1 and p322 revealed two loci, and probe He3 revealed 4 loci on the YAC contig, whereas probe 13xb4 revealed several loci on 5p and 5q13. The restriction map (FIG. 6) showed that the 5q13 region contained a large inverted duplication of an element (E) of at least 500 Kb, termed $E^{Tel}$ and $E^{Cen}$ for the telomeric and centromeric elements, respectively.

The PFGE analysis of SMA and control individuals revealed a high degree of variability of restriction fragments which hampered the distinghishment of $E^{Tel}$ from the $E^{Cen}$ and the recognition of abnormal restriction fragments in SMA patients.

In order to distinguish between the $E^{Tel}$ and the $E^{Cen}$, a Southern blot analysis was then performed. The Southern blot was performed by the methods described in Sambrook et al, supra.

More specifically, DNA from YAC clones, controls and SMA patients was digested with restriction enzymes SacI, KpnI, MspI, PstI, PvuII, EcoRI, HindIII, BgII and XbaI for Southern blotting and hybridized with clones 132SE11, 11p1, He3, 131xb4 and p322 as probes. None of the probes except one (He3) detected a difference between the two duplicated elements. Three HindIII restriction fragments of 12, 11 and 3.7 Kb were detected by probe He3. A 12 Kb HindIII restriction fragment was detected in YAC clones 754H5 and 759A3, indicating that this fragment corresponded to the most centromeric locus in the $E^{Cen}$.

Conversely, a 11 Kb HindIII fragment was detected in YACs clones 595C11, 903D1 and 920C9 indicating that this fragment corresponded to a single locus on the $E^{Tel}$. Finally, a 3.7 Kb HindIII fragment was noted in non-overlapping YACs containing either $E^{Tel}$ or $E^{Cen}$, indicating that this fragment corresponded to two different loci. Similar results were obtained with SacI and KpnI. The three restriction fragments detected by He3 were observed on the monochromosomal hybrid HHW105 (Carlock, L. R. et al, *Am. J. of Human Genet.*, 1985, Vol. 37, p. 839) and in 30 unrelated, healthy individuals, confirming that these fragments were not due to polymorphisms. The Southern analysis results allowed one to distinguish $E^{Tel}$ from the $E^{Cen}$ in both controls and SMA patients.

Thus, once the $E^{Tel}$ from the $E^{Cen}$ was distinguished, it was necessary to determine the differences between the $E^{Tel}$ in SMA patients and those of the normal control. This was done by using genetic and physical mapping. This genetic and physical mapping identified genomic rearrangements in the telomeric element of $E^{Tel}$ of SMA patients.

It was previously shown that 9 out of 201 (9/201) SMA patients displayed large-scale deletions encompassing either one or the two loci detected by markers C212 and C272 on one mutant chromosome (J. Melki et al, *Science*, 264, 1474 (1994)). On the other hand, 22 out of 30 (22/30) patients born to consanguineous parents including 13 out of 14 (13/14) type 1 and 9 out of 10 (9/10) type III SMA, were homozygous by descent for the most closely flanking polymorphic markers.

The genomic DNA of the 9 patients harboring large scale deletions and the 22 consanguineous patients displaying homozygosity by descent were digested with HindIII for Southern blotting and hybridized with probe He3. The 11 Kb fragment revealed by probe He3 was absent in 12 out of 13 (12/13) consanguineous type I patients. In 2 out of 12 (2/12), the deletion also involved the 3.7 Kb fragment. By contrast, the 11 Kb fragment was absent in 1 out of 8 (1/8) consanguineous type III patients only. Consistently, the 11 Kb HindIII fragment was absent in 4 out of 9 (4/9) patients harboring large scale deletions on one mutant chromosome. Of particular interest was the absence of the 11 Kb fragment in the patient harboring a deletion of one of the two loci detected by markers C212 and C272.

When analyzed together, these observations provided evidence for genomic rearrangements of $E^{Tel}$ in SMA patients and supported the location of the SMA gene centromeric to the locus revealed by the 11 Kb HindIII fragment, since all consanguineous type III patients but one were not deleted for this locus.

In order to characterize the centromeric boundary of the genomic rearrangement in the disease, the allele segregation at loci detected by marker C272 in consanguineous SMA patients was analyzed. All consanguineous SMA type I patients had one single PCR amplification product, compared with 0 out of 60 controls. This marked heterozygosity deficiency was due to deletion of one of the two loci detected by C272, as indicated by the marked decrease of gene dosage with probe 132SE11, mapping close to this marker. By contrast, 7 out of 9 (7/9) consanguineous type III SMA patients had two C272 amplification products inherited from both parents, indicating homozygosity at each locus detected by marker C272. Moreover, no gene dosage effect was observed with probe 132SE11 indicating the absence of deletion involving the locus detected by C272 in type III consanguineous patients.

Assuming that the same locus is involved in all three types of SMA, these results indicate that the disease causing gene is distal to the tetomeric locus detected by C272.

These studies place the SMA gene within the telomeric element $E^{Tel}$, between the telomeric loci detected by markers C272 and He3 (11 kb HindIII fragment). Based on long-range restriction mapping using PGFE of the YAC contig, this critical region is entirely contained in a 140 Kb SacII fragment of YAC clone 903D1 (or 150 Kb SacII fragment of YAC clone 920D9).

After confirming that the SMN gene was located on a 140 Kb SacII fragment a phage contig spanning the critical region of the telomeric element was constructed in order to identify and characterize the SMN gene.

Phage clones containing markers C212, C272, C171 and C161 were isolated from the ? phage libraries constructed from YAC clones 595C11 and 903D1 and used as a starting point for bidirectional walking. A phage contig (60 Kb) surrounding markers C212, C272 and C171 was constructed based on the restriction map of the phage clones (FIG. 6).

To identify genes in the contig, the following three strategies were used:

1) a search for interspecies-conserved sequences was conducted;

2) exon trapping method was performed; and 3) direct cDNA selection was performed. The genomic probe 132SE11, derived from the phage containing the marker C272, gave positive hybridization signals with hamster DNA indicating the presence of interspecies-conserved sequences. The screening of a λgt10 human fetal brain cDNA library with probe 132SE11 resulted in the selection of 7 overlapping λ clones spanning 1.6 kbp. Sequence analysis of the clones revealed a 882 bp open-reading frame (ORE) and a 580 bp non-coding region. A 1.5 kbp clone (BCD541) contained the entire coding sequence and most of the 3' non-coding region. The 3' end of the cDNA along with its poly(A)$^+$ tail was obtained by PCR-amplification of a lymphoblastoid cell line cDNA library.

Two cDNA clones lacked nucleotides 661 to 755, suggesting that an alternative splicing might have occurred. Northern blot analysis of poly(A)$^+$RNA from various tissues including heart, brain, liver, muscle, lung, kidney and pancreas, revealed the presence of a widely expressed 1.7 kb transcript. The ORF encodes a putative protein of 294 amino acids with a predicted molecular weight of approximately 32 Kd.

A homology search using the FASTA and BLAST networks failed to detect any homology at either the nucleotide or the amino acid level.

To further distinguish whether there was any duplication of the BCD541 gene in the 5q13 region, BCD541 cDNA was used as a probe for Southern blot and PFGE analysis of YAC clones spanning the disease locus.

Specific hybridization with non-overlapping YACs containing either the $E^{Cen}$ only (YAC clones 759A3, 121B8 and 278G7), or containing the $E^{Tel}$ only (YAC clone 595C11) provided evidence for duplication of the BCD541 gene. Each gene encompassed approximately 20 kb and displayed an identical restriction pattern. Evidence for head to head orientation of the two genes was derived from the location of the SacII and EagI restriction sites of the non-overlapping YAC clones containing either $E^{Cen}$ or $E^{Tel}$, following hybridization experiments with probes BCD541 end p322 which flank the SacII and EagI sites of each element.

In order to look for divergences in the two copies of the BCD541 gene, the organization of the telomeric gene was characterized and compared to that of the centromeric counterpart. Genomic sequence analysis revealed that the telomeric BCD541 gene is composed of 8 exons (FIG. 3). However, it is now known that the previously known exon 2 is composed of 2 exons separated by an additional intron as set forth in FIG. 10, therefore the SMN gene is composed of 9 exons.

Starting from either the centromeric or telomeric gene loci (in YAC clones 121B8 and 595C11, respectively), PCR-amplification and sequence of each exon and their flanking regions revealed five discrepancies between the centromeric and the telomeric BCD541 genes. The first one is a conservative substitution in exon 7 (codon 280) specific for the telomeric (TTC) or the centromeric BCD541 gene (TTT). The second one, located in the 3' non-coding region (exon 8 nucleotide n° 1155) is specific for the telomeric (TGG) or the centromeric BCD541 gene (TGA). Three other single base substitutions were observed in the sixth and seventh introns.

The observation of both versions of each exon (exon 7 and 8) on either YAC clones containing both gene loci (YAC clone 920C9) or the monochromosomal hybrid HHW105 demonstrated that these substitutions are neither allelic nor due to polymorphisms. Band shifts on SSCP analysis of amplified exons 7 and 8 allowed an easy distinction of the telomeric (T-BCD541) and centromeric genes (C-BCD541) in both controls and SMA patients. All the unrelated healthy controls tested (n=75) harbored the T-BCD541 gene as determined by SSCP analysis of exons 7 and 8 (100%). Most of them (89.3%) also harbored the C-BCD541 gene but 8 out of 75 (8/75) (10.7%) lacked the C-BCD541.

A total of 230 SMA patients were tested for single base substitutions detected in exons 7 and 8 by SSCP method after PCR-amplification of genomic DNA. Among them, 103 belonged to type I, 91 to type II, and 36 to type III. Interestingly, 213 out of 230 SMA patients (92.6%) lacked the T-BCD541 gene on both mutant chromosomes compared with 0 out of 75 controls (0%). Moreover, 13 out of 230 SMA patients (5.6%) lacked the T-BCD541 gene for exon 7 on both mutant chromosomes but retained the T-BCD541 gene for exon 8 compared with 0 out of 75 controls (0%). Finally, only 4 out of 230 SMA patients (1.7%) harbored the T-BCD541 gene as determined by SSCP analysis of exons 7 and 8.

These results show that the T-BCD541 gene is either lacking or truncated in 98% of SMA patients. In addition, these data support the view that the disease gene is located between the telomeric locus detected by C272 and exon 8 of the T-BCD541 gene. Therefore, according to the overlapping restriction map of the phage contig, the critical region is entirely contained in 20 kb, suggesting that the telomeric BCD541 gene is the chromosome 5 SMA-determining gene.

In order to demonstrate that the T-BCD541 gene is responsible for SMA, point mutations in the 4 SMA patients in whom no rearrangement of the TBCD541 gene had been observed were searched. Direct sequencing of PCR amplification products of each exon with their flanking regions was performed in the four patients.

A 7 bp deletion in the 3' splice acceptor site of intron 6 (polypyrimidine tract) was found in patient SA. Sequence analysis of exon 7 flanking the deleted intron, recognized the sequence specific for the T-BCD541 gene. Moreover, the non-deleted PCR-product corresponding to the same region, harbored the sequence specific for the C-BCD541 suggesting that the other mutant allele lacked the T-BCD541 gene.

In patient B1, a 4 bp deletion in the 5' consensus splice donor site of intron 7 was found. This deletion occurred on the T-BCD541 gene as determined by sequence analysis of the flanking exon 7.

In patient HU, a point mutation in codon 272 (TAT→TGT) was found. This mutation changed a Tyrosine to Cysteine. The patient was heterozygous for the mutation, presumably carrying a different SMA mutation on the other allele. All three mutations observed in patients SA, HU and BI were not detected in 100 normal chromosomes ruling out rare polymorphisms.

A different splicing of exon 7 distinguished the C-BCD541 from the TBCD541 gene using reverse transcription-based PCR. Eleven SMA patients were selected for the analysis of their transcripts by Northern blot or reverse transcription-based PCR amplification. Eight of them belonged to type I, I to type II and 2 to type III. SSCP analysis of genomic DNA showed an absence of T-BCD541 gene in 10 patients and one patient (SA) had C-BCD541 and TBCD541 genes for both exons 7 and 8. Six unrelated controls who harbored both C-BCD541 and T-BCD541 genes and 2 controls with only T-BCD541 gene were included in the present study.

The expression of this gene in lymphoblasts made it possible to analyze the BCD541 transcripts in cell lines derived from controls and SMA patients. Northern blot analysis of RNA from lymphoblastoid cell lines showed the presence of a 1.7 kb mRNA in all samples. None of the SMA patients showed a transcript of altered size. It was observed that a reduced level of transcripts was obtained when compared to the expression of the R-active gene in 3 out of 4 type I SMA patients. Normal mRNA level were found for the other SMA probands.

Since the Northern blot analysis revealed the presence of a transcript in SMA patients who had the C-BCD541 gene only for both exons 7 and 8 as determined by SSCP analysis, these results indicated that both C-BCD541 and T-BCD541 genes were expressed. To prove whether both BCD541 genes were expressed, RT-based PCR amplification of RNA isolated from the lymphoblastoid cell lines from controls and SMA patients was used. Direct sequencing of PCR products flanking exons 7 and 8 revealed that patients who had C-BCD541 only displayed the sequence specific for the C-BCD541 gene. Controls who had both T-BCD541 and C-BCD541 genes, had two types of transcripts corresponding to both BCD541 genes. These results confirmed that both genes were expressed. In addition, 2 alternative splicings involving exon 5 or exon 7 that resulted in different transcripts were observed. The alternative splicing of exon 5 confirmed previous sequence data on the cDNA clones.

The analysis of the RT-PCR amplification products encompassing exons 6 to 8 showed that the spliced transcript keeping exon 7, was present in controls who had both C-BCD541 and T-BCD541 genes or controls who had the T BCD541 gene only. Conversely, the alternative spliced transcript lacking exon 7 was observed in controls who had both genes, but not in controls who had the T-BCD541 gene only. These results indicated that the alternative spliced transcript lacking exon 7 was derived from the C-BCD541 gene only.

The transcript analysis of patient SA harboring a 7 bp deletion of the 3' splice acceptor site of intron 6 of the T-BCD541 gene revealed the presence of both spliced transcript keeping exon 7 and alternate spliced transcript lacking exon 7. Moreover, the sequence analysis of amplification products from the spliced transcript keeping exon 7, showed a sequence specific for the C-BCD541 gene (FIG. 2). These results demonstrated that the 7 bp deletion of intron 6 observed in patient SA was deleterious for the correct splicing of exon 7 of T-BCD541 gene only. In addition, because a differential splicing of exon 7 allowed one to distinguish the 2 BCD541 genes, this difference was analyzed among controls and SMA patients including patient SA. In controls, the amount of alternated spliced transcript lacking exon 7 was less abundant than that of spliced product keeping exon 7. Conversely, in SMA patients, the amount of alternated spliced transcript lacking exon 7 was equal or more abundant than that of spliced product keeping exon 7.

These results provide evidence for a difference between controls and SMA patients at the transcription level of these genes. The alternative spliced transcript lacking exon 7 resulted in a shorter ORF with a different C-terminus protein that might have effects on the protein function.

To further characterize the entire structure and organization of the human SMN gene, three genomic clones were isolated from a FIX II phage library derived from YAC clone 595C11 and screened with the full-length BCD541 cDNA (FIG. 2A) as a probe. After selecting several clones that hybridized to the probe, restriction mapping and Southern blot analysis indicated that phages L-132, L-5 and L-13 spanned the entire SMN gene.

These three phage clones were further subjected to sequencing using the Maxam-Gilbert or Sanger et al methods of sequencing disclosed in Sambrook et al. supra.

The nucleotide and amino acid sequence of the entire SMN gene including exons and introns is set forth in FIG. 10. The human gene is approximately 20 kb in length and consists of nine (9) exons interrupted by 8 introns as shown in FIG. 10. The human SMN gene has a molecular weight of approximately 32 kDA.

Figure 9:
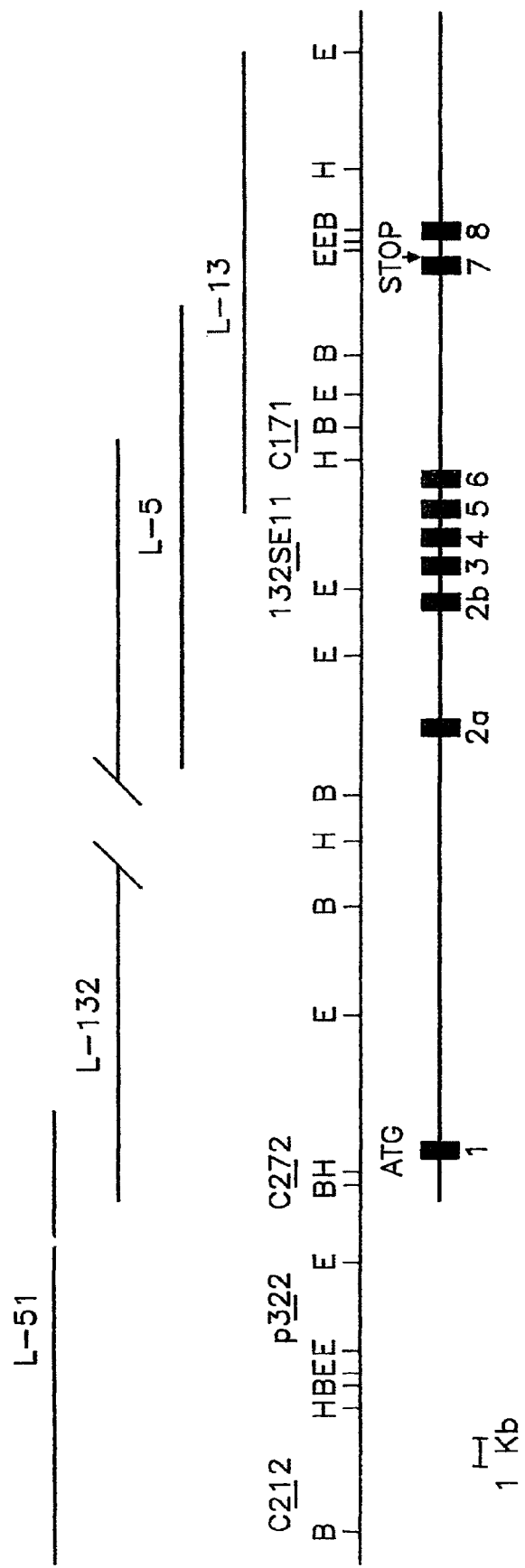
FIG. 9 is a schematic representation of the genomic structure of the human SMN gene. The designations and positions of genomic clones are shown above the figure. L-132, L-5, and L-13 depict the genomic clones spanning the entire SMN gene, while L-51 spans part of exon 1. Micro satellites and DNA markers are indicated above the genomic map. B, H, and E mean BgIII, HindIII and EcoRI, respectively. C212, p322, C272, 132SEII and C171 represent various markers. 1, 2a, 2b, 3, 4, 5, 6, 7, and 8 represent exons of the SMN and C-BCD541 genes. The entire sequence of L-132 is obtained by PCR amplification from exon 1 to exon 2A.

Although it was thought that only one exon 2 was present in the SMN gene (see, Lefebvre et al., Cell, 80:155-165 (1995)), the sequencing data proved otherwise and the previously mentioned exon 2 in Lefebvre et al., supra is in fact composed of 2 exons separated by an additional intron, as illustrated in FIGS. 9 and 10. To avoid confusion in the renumbering of exons, the 2 exons in exon 2 are now referred to as exon 2a and exon 2b.

All exon-intron bounderies displayed the consensus sequence found in other human genes and a polyadenylation consensus site is localized 550 bp downstream from the stop codon (FIG. 10).

Figure 15:
FIG. 15 illustrates the band shifts on single strand confirmation polymorphism (SSCP) analysis of the PCR amplified intron 7 and permitted identification of SMN (closed arrowheads) and its centromeric counterpart C-BCD541 (open arrowheads).

Starting from either YAC clones 121B8 or 595C11 (which contain the C-BCD541 and SMN genes respectively, (see, Lefebvre et al., supra) PCR amplification and sequence analysis of the introns showed three differences between SMN and C-BCD541 in addition to those previously described (by Lefebvre et al., supra). These included a base charge in intro 6 (−45 bp/exon 7, atgt, telomeric, atat, centromeric) and two changes in intron 7 (+100 bp/exon 7, ttaa, telomeric; ttag, centromeric and at position +214 bp/exon 7, ttat, telomeric; ttgt, centromeric, FIG. 10). The presence of both versions in a YAC clone containing both genes (YAC 920C9), and in the control population demonstrated that these substitutions are locus-specific rather than due to polymorphism. Band shifts on single strand conformation polymorphism (SSCP) analysis of the PCR amplified intron 7 allowed SMN and its centromeric counterpart (C-BCD541) to be readily distinguished (see, FIG. 15).

In order to identify sequences potentially important for promoter function, the organization of the region surrounding exon 1 of the SMN and C-BCD541 genes was characterized. Based on restriction mapping, Southern blot hybridization and PCR amplification, exon 1 and the C272 marker (D5F150S1, D5F150S2) were located in the same BgIII-EcoRI restriction fragment of L-132 phage (FIG. 9). PCR amplification using the C272f primer and a reverse primer chosen in exon 1 was performed and the amplified product was directly sequenced. Sequence analysis showed that the (CA) repeat corresponding to the C272 marker are located 463 bp upstream from the putative ATG translation start site (FIG. 11). Comparative sequence analyses showed no discrepancy between the 5' ends of the SMN gene and its centromeric counterpart (C-BCD541). In addition, sequence analysis showed the presence of putative binding sites for the following transcription factors: AP-2, GH-CSE2, DTF-1, E4F1, HiNF-A, H4TF-1, β-IFN, Sp1 (FIG. 11; Faisst et al, Nucleic Acids Res., 20:3-26 (1992)).

Besides isolating and characterizing the human SMN gene, the mouse homologue of the SMN gene was also cloned. Cross-species conservation of human SMN gene with rodents has been shown in Lefebvre et al., supra and served to isolate the mouse SMN gene. Screening of a mouse fetal cDNA library using human SMN cDNA as a probe allowed the isolation of 2 overlapping mouse cDNA clones. Sequences analysis of the clones revealed an 864 bp open-reading frame (ORF) (FIG. 12). The ORF encodes a putative protein of 288 amino acids (FIG. 12) with an homology of 83% with human SMN amino acid sequence (FIG. 13).

Either the isolated human or the mouse SMN, the gene can be inserted into various plasmids such as pUC18, pBr322, pUC100, λgHI, λ18-23, λZAP, λORF8, and the like. The methods for inserting genes into different plasmid vectors are described by Sambrook et al., supra. Various microorganisms can be used to transform the vector to produce the SMN gene. For example, host microorganisms include, but are not limited to, yeast, CHO cells, *E. coli, Bacillus subtilis* and the like.

Once recombinantly produced, the human SMN protein or the mouse SMN protein can be further purified from the host culture by methods known in the art.

Besides recombinantly producing the SMN protein, the present invention also relates to the production of polyclonal and monoclonal antibodies. These methods are known in the art as evidenced by Sambrook et al. supra. The monoclonal antibody can be obtained by the procedure of Kohler and Milstein, *Nature,* 256:495 (1975); Eur. J. Immunol 6:511 (1976) or Harlow and Lane *Antibodies*, a Laboratory Manual, Cold Spring Harbor Laboratory, Cold Spring Harbor, N.Y. (1988), and can be used, for example, in diagnosing SMA, as well as other motor neuron disorders.

Polyclonal rabbit antisera can also be generated against synthetic peptides corresponding to any part of the SMN amino acid sequence including the amino terminus and carboxy terminus. More specifically, the following peptides were synthesized based on the amino acid sequence set forth in FIG.1:

```
N-terminal      G G V P E Q E D S V L F R R G T
                (residues 10-25 of SEQ ID NO: 9)

C-terminal      S R S P G N K S D N I K P K
                (residues 173-186 of SEQ ID NO: 9)

F R Q N Q K E G R C S H S L N
                (residues 280-294 of SEQ ID NO: 9)
```

The synthetic peptide may be coupled to a carrier protein such as Keyhole limpet hemocyanin (KLH) through an amino- or carboxy-artificial cysteine residue that may be synthetically added to the desired sequence. The cysteine residue is used as a linker to couple the synthetic peptide to the carrier protein. The procedure utilized to couple synthetic peptides to KLH is described by Green et al., *Cell*, 28:477 (1982).

Approximately, 50-100 µg, preferably 100 µg of synthetic antigen is dissolved in buffer and emulsified with an equal volume of Freund's complete adjuvant. About 0.025 ml to 0.5 ml of emulsified antigen-adjuvant can be injected intramuscularly or intradermaly into a rabbit. Four to six weeks later, the rabbit is boosted and 20-40 ml of blood is drawn 7-10 days after each booster injection. The serum is then tested for the presence of antigen using RIA, ELISA or immunoprecipitation. The positive antibody fractions may then be purified, for example by absorption to protein A following the method of Goudswaald at al., *Scand. J. Immunol.*, 8:21 (1978).

More specifically, about 20 to 50 µg of antigen, prepared either by the recombinant techniques set forth above or synthetically made antigen is diluted in about 100 µl of buffer and emulsified with an equal amount of Freund's complete adjuvant. About 30-60, preferably 50 µl of the emulsified antigen-adjuvant is injected subcutaneously at four sites into mice. Four to six weeks later, the mice are boosted with an intraperitoneal injection of about 100 µl containing 5-10 µg of antigen solubilized in buffer. The mice are bled from the medium tail vein 7-10 days after the boaster injection and the serum is tested for antibody using standard methods. Blood is then drawn every 3-4 days until the antibody titer drops.

Tissue, plasma, serum, cerebral spinal fluid and the like can be used to detect SMA disease using the above-described monoclonal or polyclonal antibodies via Western blot (1 or 2 dimensional) or ELISA. These methods are known in the art as described by Sambrook et al., supra.

A method for detecting SMA as well as in ALS, ACM, and PLS patients who possibly have these motor neuron disorders, is also encompassed by the present invention. This method involves extracting from a patient suspected of having SMA, DNA from a sample. This sample may include sera, plasma, cerebral spinal fluid and the like. After extracting the DNA by known methods in the art, primers that are derived from exons 7 and 8 of the SMN gene are used to amplify the DNA.

After amplification with the primer, the amplified product is subjected to SSCP (Single Strand Conformation Polymorphism).

The gels are then subjected to autoradiography to determine if SMA is present in the sample.

More specifically, it has recently been discovered that in twelve cases of arthrogryposis multiplex congenita (AMC) associated with SMA, 6 out of 12 patients lacked the SMN gene.

A total of twelve unrelated patients including eight males and four females of various geographic origins was selected for the study. The patients were chosen based on the criteria that these patients had:

(1) congenital joint contractures of at least two regions of the body (see, Stern, JAMA, 81:1507-1510 (1923));
(2) generalized muscle weakness with muscular atrophy and areflexia without extraocular involvement;
(3) electromyographic studies showed denervation and diminished motor action potential amplitude; and
(4) muscle biopsies consistent with denervation with no evidence of storage material or other structural abnormalites (see, Munsat, *Neuromuscular Disorders,* 1:81 (1991)).

The study consisted of Dinucleotide Repeat Polymorphism Analysis and SMN gene analysis (see, Examples) based on DNA extracted from peripheral blood leukocytes, lymiphoblastoid cell lines or muscle tissue in all twelve patients.

The data from this study is summarized in Table 1 below.

The diagnosis was made at birth with an uniform phenotype character Iced by a severe hypotonia, absence of movements except extraocular mobility and contractures of at least two joints. The number of affected joints and the severity of the postural defects varied from infant to infant, as set forth in Table 1. Decreased fetal movements were noted in 7 out of 12 (7/12) patients. Neonatal respiratory distress was observed in 9 out of 12 (9/12) patients and facial involvement associated with micrognathia was noted in 4 out of 12 (4/12) patients. Most of the cases, 8 out of 12 (8/12), died within the first month of life. Four infants are still alive. No family history was noted except in family 12 in which both the child and her father were affected suggesting an autosomal dominant form of AMC.

Figure 14A:
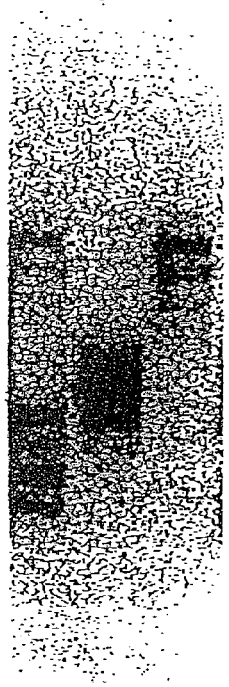
FIGS. 14A-C illustrates the genetic analysis of family 6. Lane A shows evidence of inherited maternal deletion seen with the microsatellite marker C272 as the proband inherited only allele from the father. Lanes B and C represent SSCP analysis of PCR-amplified exons 7 (lane B) and 8 (lane C) of SMN (closed arrowheads) and its centromeric copy (open arrowheads). "F" represents the father, "M" the mother, "A" the affected infant.
Figure 14B:
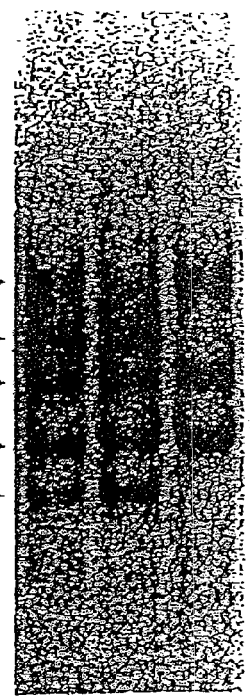
Figure 14C:
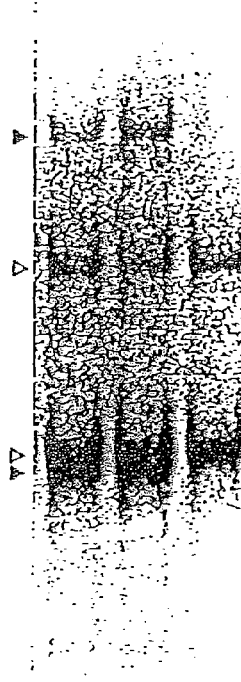

Table 1 shows that the SMN gene was lacking on both mutant chromosomes in 6 out of 12 (6/12) patients (cases 1-6). Among them, 3 out of 6 (3/6) patients had a large inherited deletion involving both loci detected by markers C212 and C272 on one parental allele, the other parental carrying only one locus instead of the expected two, as shown in FIG. 14.

Analysis of SMN exons did not reveal intragenic mutations in the patients whose SMN gene showed no deletions (cases 7-12). Genetic analysis showed that the disease gene in a family (case 9) was not linked to chromosome 5q13 as both the affected and healthy siblings carried the same 5q13 haplotype. These data strongly suggest that the patients whose SMN gene showed no deletions were not linked to the 5q13 SMA locus (cases 7-12).

Hitherto, arthrogryposis was regarded as an exclusion criterion in SMA (sec, Munsat, supra). But the observation of SMN gene deletion in 6 out of 12 (6/12) patients (50%) strongly indicates that arthrogryposis of neurogenic origin is related to SMA and that this subgroup and SMA are allelic disorders. Yet, AMC of neurogenic origin is a genetically heterogeneous condition since the disease gene was not linked to SMN locus in 6 out of 12 (6/12) patients. Exclusion of chromosome 5q has also been shown in one family with two AMC-SMA patients, as described by Lunt et al., J. Med. Genet., 29:273 (Abstract) (1992).

Thus, by dinucleotide Repeat Polymorphism Analysis and SMN gene analysis, clinical diagnosis of AMC can be confirmed by the absence or interruption of the SMN gene. The present invention now provides methods to detect AMC either in live patients or in utero.

Yet another embodiment of the present invention is the detection of SMA using specific oligonucleotide probes based on the nucleotide sequence set forth in FIGS. 3, 10, or for the mouse SMA FIG. 12. If a patient totally is lacking in the SMN gene, no hybridization to the specific probe will occur. The hybridization conditions may vary depending upon the type of sample utilized. It is preferable to conduct such hybridization analysis under stringent conditions which are known in the art and defined in Sambrook et al supra. The oligonucleotide probes may be labeled in any manner such as with enzymes, radioactivity and the like. It is preferable to use radiolabeled probes.

In another embodiment of the present invention, the human SMN gene can be utilized in conjunction with a viral or non-viral vector for administration in vivo directly to the patients suffering from SMA or related motor neuron diseases or by administration in vitro in bone marrow cells, epithelial cells fibroplasts, followed by administration to the patient. See, for example Resenfeld et al., *Science* (1991) 252, pp. 431 to 434.

The present invention provides a method of detecting SMN gene defects or the total lack of the SMN gene in a fetus. Amniotic fluid taken from the pregnant woman is subjected to SSCP analysis according to the methods of the present invention.

In order to further illustrate the present invention and advantages thereof, the following specific examples are given, it being understood that the same are intended only as illustration and in nowise limitative.

EXAMPLES

Example 1

Construction of Phage Libraries from the 121B8, 595C11, and 903D1 YAC clone.

Total yeast DNA from YAC clone 595C11 containing the telomeric loci detected by C212, C272 and C161, or YAC clone 121B8 containing the centromeric loci detected by the same markers or 903D1 YAC clone containing both loci was purified and partially digested with Sau3A. DNA in the size range of 12 to 23 kb was excised after 0.5% Seaplaque GTG agarose gel electrophoresis and precipitated with ethanol after β-agarase digestion. After partial fill-in of the Sau3A site, DNA was subcloned at the partially filled XhoI site of bacteriophage FIXIII (Stratagene). Clones of λ. containing the microsatellite DNA markers C212 (L-51), C272 (L-51, L-132), C171 (L-5, L-13), C161 (595B1), 11 M1 (L-11), AFM157xd10 (L-131) were digested either with EcoRI or HindIII or both and subcloned into pUC18 plasmid vectors. Subclones from phages containing markers C212(p322), C272(132SE11), C161(He3), AFM157xd10(131xb4) and CMS1(p11M1) were used as probes.

Example 2

Pulsed Field Gel Electrophoresis Analysis

High molecular weight DNA was isolated in agarose plugs from Epstein-Barr virus transformed lymphoblastoid cell lines established from controls and patients or from YAC clone as described. Plugs were rinsed twice for 30 min. each in 10-20 min vol. TE. The plugs were equilibrated for 30' at 4° C. with 0.3 ml of the appropriate restriction enzyme buffer containing 0.1 mg/ml BSA (Pharmacia). Excess buffer was then removed and the plugs were incubated at the appropriate temperature for 16 h with 40 U restriction enzyme per reaction. DNA was digested with the restriction enzymes BssHII, EagI, SfiI, Sad KpnI, SacII, SpeI. Separation of DNA fragments was performed using a CHEF-III-DR PFGE apparatus (Biorad). Fragments from 50 to 1200 kb were separated by electrophoresis through 1% agarose Seakerm, at 200 V for 24 h at 14° C. in 0.5×TBE running buffer using a 30' to 70' ramping pulse time. The separation of fragments from 5 to 100 kb was performed by electrophoresis at 200 V for 19 h at 14° C. in 0.5×TBE buffer using a 5' to 20' ramping pulse time. After treatment with 0.25N HCl for 20 min, pulsed field gels were blotted onto Hybond N+Nylon membrane (Amersham) in 0.4N NaOH, 0.4M NaCl for 20 h. Probes were successively hybridized to the same filters to ensure accurate data. Hybridizations were performed as described.

Example 3

YAC Library Screening

YAC libraries from CEPH were screened by PCR with microsatellites C212, C272, C171, CMS1, and C161. YAC genotypes were established by electrophoresis of PCR products on denaturing polyacrylamide gels. YAC size was estimated by pulsed field gel electrophoresis.

Example 4

Southern Blot Analysis

DNA samples were extracted from either peripheral blood leukocytes or lymphoblastoid cell lines. DNA were digested with restriction enzymes EcoRI, HindIII, BgII, XbaI, PvuII, XmnI, RsaI, PstI, BamHI, separated by electrophoresis on an 0.8% agarose gel for Southern blotting and hybridized with radioactively labeled probes.

Example 5

Dinucteotide Repeat Polymorphisms

Genotypic data were obtained for the C212(D5F149S1, -S2), C272(D5F150S1, -S2) and C161(D5F153S1, -S2) dinucleotide repeat. Amplification conditions were as follows: denaturation at 94° C., annealing at 55° C., and extension at 72° C., 1 min each for 30 cycles. The procedure used for detection of dinucleotide repeat polymorphisms has been described elsewhere.

Example 6 cDNA Clone and DNA Sequencing

Two million recombinants of a λgt10 human fetal brain library were plated according to the manufacturer (Clontech). Prehybridization and hybridization was carried out in 10% Dextran Sulphate Sodium, 1 M NaCl, 0.05 M Tris-HCl pH 7.5, 0.005 M EDTA and 1% SDS with 200 mg/ml sheared human placental DNA (Sigma) for 16 hours at 65° C. The filters were washed in 0.1×SSEP-0.1% SDS at 65° C. and autoradiographs were performed for 24 hours. The DNA of positive cDNA clones were purified, digested with EcoRI and subcloned in M13 bacteriophage. Single strand DNAs were sequenced using the DyeDeoxy™ Terminator Cycle Sequencing Kit protocol supplied by Applied Biosystems, Inc. and analyzed on a ABI model 373A DNA automated sequencer. To obtain the 3' end of the cDNA along with its poly(A)$^+$ tail, PCR-amplification of a lymphobtastoid cell line cDNA library was performed using specific primer complementary to the 3' end of the clones and primer specific to the vectors arms of the cDNA library as previously described (Fournier B., Saudubray J. M., Benichou B. et al, 1994, *J. Clin. Invest.* 94:526-531). Specific PCR-products were directly sequenced with both primers using the DyeDeoxy™ Terminator Cycle Sequencing Kit protocol supplied by Applied Biosystems, Inc. and analyzed on a ABI model 373A DNA automated sequencer.

Example 7

Isolation of RNA and Northern Blot Analysis mRNA from lymphoblast cell lines of controls and SMA patients were isolated with the QuickPrep mRNA purification kit (Pharmacia) according to the supplier's procedure. Total RNA was prepared following the single-step RNA isolation method described by Chomczynski and Sacchi (*Analytic Biochemistry*, 162:156-159 (1987)). The total RNA preparation was treated with RQ1-DNAse (Promega) to remove any contaminating genomic DNA. Northern blots were made from mRNA and total RNA by electrophoresis through 1.5% seakem agarose gel containing methyl mercuric hydroxide and transferred to positively charged membrane in 20×SSC and heated for 2 hours at 80° C. $^{32}$P-radiolabeled DNA probes were synthesized by a random priming method according to the manufacturer (Boehringer), and hybridized in a solution containing 5×SSEP, 1% SDS, 5×Denhardt's for 16 hours at 65° C. The membranes were washed to a final stringency of 0.1×SSEP, 0.1% SDS at 65° C. for 10 min. Autoradiography was at −80° C. with intensifying screens and Kodak XAR films for 2 to 10 days. The amount of mRNA was normalized with a b-actine cDNA probe. The autoradiographs were scanned at 600 nm in computerized densitometer (Hoeffer Scientific Instruments, San Francisco). A Northern blot with polyA$^{+}$ RNA from several hums tissues was purchased from Clontech.

Example 8

Reverse Transcriptase-Based PCR Amplification and Sequencing

Each PCR amplification was carried out in a final volume of 20 ml on single-strand cDNAs synthesized from the random hexamers-primed reverse transcription (Promega). The PCR reactions included 2 picomoles of forward and reverse primers and 1 unit Taq pelymerase in the reaction buffer recommended by Perkin Elmer/Cetus. Parameters for PCR amplification consisted in 1 min at 94° C., 1 min at 55° C. and 1 min at 72° C. for 30 cycles followed by a final extension period of 10 min at 72° C. Parameters for PCR amplification consisted in 1 min at 94° C., 1 min at 55° C. and 1 min at 72° C. for 30 cycles followed by a final extension period of 10 min at 72° C. The PCR products were cut from acrylamide gel and eluted in 100 ml of TE buffer. The diluted fragments were reamplified with the same primers prior direct sequencing. The PCR amplification products were cut from acrylamide gel and eluted in 100 ml of TE buffer. The diluted fragments were reamplified prior to direct sequencing with both primers using the DyeDeoxy™ Terminator Cycle Sequencing Kit protocol supplied by Applied Biosystems, Inc. and analyzed on a ABI model 373A DNA automated sequencer. Six sets of primers along the cDNA sequence were used to amplify DNA products for sequence analysis.

Example 9

Computer-Assisted Analysis

Sequence homology analysis with both nucleotide and protein sequences from 541C were performed using FASTA and BLAST through the CITI2 French network (Dessert P., Fondrat C., Velencien C., Mugnoer C., 1990, CABIOS; 6:355-356).

Example 10

SSCP Analysis

For single strand conformation polymorphism (SSCP) analysis, DNA from peripheral leukocytes (200 ng) was submitted to PCR amplification using unlabelled primers (20 μM) in 25 μl amplification mixture containing 200 μM dNTPs, 1 unit of Taq polymerise (Gibco-BRL) and 0, μl of a $^{32}$P dCTP (10 mCi/ml, NEN). Amplified DNA was mixed with an equal volume of formamide loaded dye (95% formamide, 20 mM EDTA, 0.05% bromophenol blue, 0.05% xylene cyanol). The samples (5 μl) were denatured for 10 nm at 95° C. and loaded onto a polyacrylamide gel (Hydroling MED, Bioprobe) and electrophoresed at 4° C. for 18 to 24 hours at 4 W. Gels were transferred onto 3 MM Whatman paper, dried and autoradiographed with Kodak X-OMAT films for 24 hours. To amplify the DNA sequence containing the divergence of exon 7 oligonucleotides 8111 (5' AGACTATCAACTTAATTTCTGATCA 3') and 541 C770 (SEQ ID NO:5) (5'°°TAAGGAATGTGAGCACCTTCCTTG 3') (SEQ ID NO:6) were used. To amplify the DNA sequence containing the divergence of exon 8 oligonucleotides 541 C960 (5' GTAATAACCAAATGCAATGTGAA 3') (SEQ ID NO:7) and 541C1120 (5'CTACAACACCCTTCTCACAG 3')) (SEQ ID NO:8) were used.

Example 11

Cloning of the Human SMN Gene

Total yeast DNA from YAC clone 595C11 was purified via the method of Sambrook et al., supra and partially digested with restriction enzyme Sau3A DNA in the 12-23 kD size range was excised after 0.5% sea plague GTG agarose gel electrophoresis and precipitated with ethanol after (β-agarase digestion. After partial fill-in of the Sau3A site, DNA was subcloned at the partially filled XhoI site of bacteriophage FIXII (Stratagene).

The full-length BCD541 cDNA was used as a probe to screen the FIXII phage library under conditions set forth in Sambrook et at, supra.

These phages, named M-132, L-5 and L-13 spanned the entire SMN gene as confirmed by restriction mapping using HindIII, EcoRI and BgIII (see, FIG. 9) and Southern blot analysis.

The phages were then sequenced as described in Example 8. Once the gene was sequenced, it was then cloned into a pUC18 vector and recombinantly reproduced in large quantities that were purified for further use.

Example 12

Cloning of the Mouse SMN Gene

A mouse fetal cDNA library was screened using the coding sequence of the human SMN cDNA as a probe according to Sambrook et al, supra.

Two overlapping mouse cDNA clones were found that had the entire sequence of mouse SMN, as revealed by sequencing methods described in Example 8 after being cloned into a pUC18 vector and M13 vectors.

Example 13

Transgenic Mouse

Transgenic mice containing multiple normal SMN genes OR SMN genes lacking exon 7 are produced by the methods according to Lee et al., *Neuron*, 13; 978-988 (1994). The transgenic animals are then tested and selected for the overexpression of the SMN gene or SMN gene lacking exon 7 via Southern, and/or Northern blots using the probes described in the present invention or by screening with antibodies described in the present invention in a Western blot.

Transgenic mice containing abnormal SMN genes are obtained by homologous recombination methods using mutated SMN genes as described by Kuhn et al, *Science*, 269; 1427-1429 (1995) and Bradley, *Current Opinion in Biotechnology*, 2; 823-829 (1991). The transgenic animals are then tested and selected for the overexpression of the SMN gene via Southern, and/or Northern blots using the probes described in the present invention or by screening with antibodies described in the present invention in a Western blot selected for the abnormal SMN gene.

Example 14

Polyclonal Antibodies
100 pg of a synthetic antigen having sequence :

```
N-terminal    GGVPEQEDSVLFRRGT
              (residues 10-25 of SEQ ID NO: 9)

C-terminal
``` was dissolved in buffer and emulsified with an equal volume of Freund's complete adjuvant. 0.5 ml of the emulsified synthetic antigen-adjuvant was injected intramuscularly into a rabbit. Five weeks later, the rabbit was boosted and 20-40 ml of blood was drawn 8 days after each booster injection. The serum was then tested for the presence of antigen using RIA.

Polyclonal antibodies were also prepared by the same methods using the following synthetic antigens:

```
N-terminal    S R S P G N K S D N I K P K
              (residues 173-186 of (SEQ ID NO: 9)

C-terminal    F R Q N Q K E G R C S H S L N
              (residues 280-299 of SEQ ID NO: 9)
```

Example 15

Gene Therapy
Using the adenovirus construct described by Ragot et at, *Nature*, Vol. 361 (1993), the normal SMN gene was inserted therein and injected intramuscularly into a patient lacking this gene. The patient is monitored using SSCP analysis as described in Example 10 above.

While the invention has been described in terms of various preferred embodiments, the skilled artisan will appreciate that various modifications, substitutions, omissions and changes may be made without departing from the spine thereof. Accordingly, it is intended that the scope of the present invention be limited solely by the scope of the following claims, including equivalents thereof.

What we claim is:

1. A monoclonal or polyclonal antibody directed against a human survival motor neuron protein consisting of the amino acid sequence of SEQ ID NO: 9 or a truncated amino acid sequence of SEQ ID NO: 9 or an antigen binding fragment thereof.

2. A monoclonal or polyclonal antibody directed against a human survival motor neuron protein consisting of the amino acid sequence of SEQ ID NO: 19 or an antigen binding fragment thereof.

3. A monoclonal or polyclonal antibody or antigen binding fragment thereof directed against a murine survival motor neuron protein consisting of the amino acid sequence encoded by the nucleic acid sequence of SEQ ID NO: 20.

4. A monoclonal or polyclonal antibody directed against the peptide consisting of from amino acid 10 to amino acid 25 of SEQ ID NO: 9 or an antigen binding fragment thereof.

5. A monoclonal or polyclonal antibody directed against the peptide consisting of from amino acid 173 to amino acid 186 of SEQ ID NO: 9 or an antigen binding fragment thereof.

6. A monoclonal or polyclonal antibody directed against the peptide consisting of from amino acid 280 to amino acid 294 of SEQ ID NO: 9 or an antigen binding fragment thereof.

* * * * *

SEQUENCE LISTING

```
<160> NUMBER OF SEQ ID NOS: 65

<210> SEQ ID NO 1
<211> LENGTH: 347
<212> TYPE: DNA
<213> ORGANISM: Homo sapiens

<400> SEQUENCE: 1 aattttaaa tttttgtag agacagggtc tcattatgtt gcccagggtg gtgtcaagct      60
ccaggtctca agtgatcccc ctacctccgc ctcccaaagt tgtgggattg taggcatgag     120
ccactgcaag aaaaccttaa ctgcagccta ataattgttt tctttgggat aactttaaa     180 gtacattaaa agactatcaa cttaatttct gatcatattt tgttgaataa aataagtaaa    240
atgtcttgtg aacaaaatgc tttttaacat ccatataaag ctatctatat atagctatct    300
atgtctatat agctattttt tttaacttcc ttttattttc cttacag                  347

<210> SEQ ID NO 2
<211> LENGTH: 444
<212> TYPE: DNA
<213> ORGANISM: Homo sapiens

<400> SEQUENCE: 2
gtaagtctgc cagcattatg aaagtgaatc ttacttttgt aaaactttat ggtttgtgga     60
aaacaaatgt ttttgaacag ttaaaaagtt cagatgttaa aaagttgaaa ggttaatgta    120
aaacaatcaa tattaaagaa ttttgatgcc aaaactatta gataaaaggt taatctacat    180
ccctactaga attctcatac ttaactggtt ggttatgtgg aagaaacata ctttcacaat    240
aaagagcttc aggatatgat gccattttat atcactagta ggcagaccag cagactttt     300 tttattgtga tatgggataa cctaggcata ctgcactgta cactctgaca tatgaagtgc    360
```

```
tctagtcaag tttaactggt gtccacagag gacatggttt aactggaatt cgtcaagcct    420
ctggttctaa tttctcattt gcag                                           444

<210> SEQ ID NO 3
<211> LENGTH: 347
<212> TYPE: DNA
<213> ORGANISM: Homo sapiens

<400> SEQUENCE: 3
aatttttaaa ttttttgtag agacagggtc tcattatgtt gcccagggtg gtgtcaagct     60
ccaggtctca agtgatcccc ctacctccgc ctcccaaagt tgtgggattg taggcatgag    120
ccactgcaag aaaaccttaa ctgcagccta ataattgttt tctttgggat aacttttaaa    180
gtacattaaa agactatcaa cttaatttct gatcatattt tgttgaataa aataagtaaa    240
atgtcttgtg aacaaaatgc ttttttaacat ccatataaag ctatctatat atagctatct    300
atatctatat agctattttt tttaacttcc ttttatttc cttacag                   347

<210> SEQ ID NO 4
<211> LENGTH: 444
<212> TYPE: DNA
<213> ORGANISM: Homo sapiens

<400> SEQUENCE: 4
gtaagtctgc cagcattatg aaagtgaatc ttacttttgt aaaactttat ggtttgtgga     60
aaacaaatgt ttttgaacag ttaaaaagtt cagatgttag aaagttgaaa ggttaatgta    120
aaacaatcaa tattaaagaa ttttgatgcc aaaactatta gataaaaggt taatctacat    180
ccctactaga attctcatac ttaactggtt ggttgtgtgg aagaaacata ctttcacaat    240
aaagagcttt aggatatgat gccatttat atcactagta ggcagaccag cagacttttt     300
tttattgtga tatgggataa cctaggcata ctgcactgta cactctgaca tatgaagtgc    360
tctagtcaag tttaactggt gtccacagag gacatggttt aactggaatt cgtcaagcct    420
ctggttctaa tttctcattt gcag                                           444

<210> SEQ ID NO 5
<211> LENGTH: 25
<212> TYPE: DNA
<213> ORGANISM: Artificial Sequence
<220> FEATURE:
<223> OTHER INFORMATION: R111 primer/probe characteristic of exon 7 of
      the T-BCD541 gene.

<400> SEQUENCE: 5
agactatcaa cttaatttct gatca                                           25

<210> SEQ ID NO 6
<211> LENGTH: 24
<212> TYPE: DNA
<213> ORGANISM: Artificial Sequence
<220> FEATURE:
<223> OTHER INFORMATION: 541C770 primer/probe characteristic of exon 7
      of the T-BCD541 gene.

<400> SEQUENCE: 6
taaggaatgt gagcaccttc cttc                                            24

<210> SEQ ID NO 7
<211> LENGTH: 23
<212> TYPE: DNA
<213> ORGANISM: Artificial Sequence
<220> FEATURE:
```

-continued

<223> OTHER INFORMATION: 541C960 primer/probe characteristic of exon 8
      of the T-BCD541 gene.

<400> SEQUENCE: 7
gtaataacca aatgcaatgt gaa                                           23

<210> SEQ ID NO 8
<211> LENGTH: 20
<212> TYPE: DNA
<213> ORGANISM: Artificial Sequence
<220> FEATURE:
<223> OTHER INFORMATION: 541C1120 primer/probe characteristic of exon 8
      of the T-BCD541 gene.

<400> SEQUENCE: 8
ctacaacacc cttctcacag                                               20

<210> SEQ ID NO 9
<211> LENGTH: 294
<212> TYPE: PRT
<213> ORGANISM: Homo sapiens

<400> SEQUENCE: 9

```
Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Gly Phe Arg Gln Asn Gln Lys Glu Gly Arg
```

```
              275                 280                 285
Cys Ser His Ser Leu Asn
    290

<210> SEQ ID NO 10
<211> LENGTH: 1582
<212> TYPE: DNA
<213> ORGANISM: Homo sapiens

<400> SEQUENCE: 10
cggggcccca cgctgcgcac ccgcgggttt gctatggcga tgagcagcgg cggcagtggt    60
ggcggcgtcc cggagcagga ggattccgtg ctgttccggc gcggcacagg ccagagcgat   120
gattctgaca tttgggatga tacagcactg ataaaagcat atgataaagc tgtggcttca   180
tttaagcatg ctctaaagaa tggtgacatt tgtgaaactt cgggtaaacc aaaaaccaca   240
cctaaaagaa aacctgctaa gaagaataaa agccaaaaga gaatactgca gcttcctta    300 caacagtgga aagttgggga caaatgttct gccatttggt cagaagacgg ttgcattta    360 ccagctacca ttgcttcaat tgattttaag agagaaacct gtgttgtggt ttacactgga   420
tatgaaaata gagaggagca aaatctgtcc gatctacttt ccccaatctg tgaagtagct   480
aataatatag aacagaatgc tcaagagaat gaaaatgaaa gccaagtttc aacagatgaa   540
agtgagaact ccaggtctcc tggaaataaa tcagataaca tcaagcccaa atctgctcca   600
tggaacccct ttctccctcc accacccccc atgccagggc aagactggga ccaggaaag   660 ccaggtctaa aattcaatgg cccaccaccg ccaccgccac caccaccacc ccacttacta   720
tcatgctggc tgcctccatt tccttctgga ccaccaataa ttcccccacc acctcccata   780
tgtccagatt ctcttgatga tgctgatgct ttgggaagta tgttaatttc atggtacatg   840
agtggctatc atactggcta ttatatgggt tttagacaaa atcaaaaaga aggaaggtgc   900
tcacattcct taaattaagg agaaatgctg gcatagagca gcactaaatg acaccactaa   960
agaaacgatc agacagatct ggaatgtgaa gcgttataga agataactgg cctcatttct  1020
tcaaaatatc aagtgttggg aaagaaaaaa ggaagtggaa tgggtaactc ttcttgatta  1080
aaagttatgt aataaccaaa tgcaatgtga atatttac tggactcttt tgaaaaacca  1140
tctgtaaaag actgaggtgg gggtgggagg ccagcacggt ggtgaggcag ttgagaaaat  1200
ttgaatgtgg attagatttt gaatgatatt ggataattat tggtaatttt atggcctgtg  1260
agaagggtgt tgtagtttat aaaagactgt cttaatttgc atacttaagc atttaggaat  1320
gaagtgttag agtgtcttaa aatgtttcaa atggtttaac aaaatgtatg tgaggcgtat  1380
gtggcaaaat gttacagaat ctaactggtg gacatggctg ttcattgtac tgttttttc  1440 tatcttctat atgtttaaaa gtatataata aaaatattta attttttttt aaaaaaaaa  1500 aaaaaaaaaa aaaaaaaaaa aaaaaaaaaa aaaaaaaaa aaaaaaaaaa aaaaaaaaa  1560 aaaaaaaaaa aaaaaaaaa aa                                           1582

<210> SEQ ID NO 11
<211> LENGTH: 1408
<212> TYPE: DNA
<213> ORGANISM: Homo sapiens

<400> SEQUENCE: 11 aattttaaa ttttttgtag agacagggtc tcattatgtt gcccagggtg gtgtcaagct     60
ccaggtctca agtgatcccc ctacctccgc ctcccaaagt tgtgggattg taggcatgag   120
ccactgcaag aaaaccttaa ctgcagccta ataattgttt tctttgggat aacttttaaa   180
```

-continued

```
gtacattaaa agactatcaa cttaatttct gatcatattt tgttgaataa aataagtaaa    240
atgtcttgtg aacaaaatgc ttttaacat ccatataaag ctatctatat atagctatct     300
atatctatat agctattttt tttaacttcc tttattttc cttacagggt tttagacaaa     360
atcaaaaaga aggaaggtgc tcacattcct taaattaagg agtaagtctg ccagcattat    420
gaaagtgaat cttacttttg taaaacttta tggtttgtgg aaaacaaatg tttttgaaca    480
gttaaaaagt tcagatgtta gaaagttgaa aggttaatgt aaaacaatca atattaaaga    540
attttgatgc caaaactatt agataaaagg ttaatctaca tccctactag aattctcata    600
cttaactggt tggttgtgtg gaagaaacat actttcacaa taaagagctt taggatatga    660
tgccatttta tatcactagt aggcagacca gcagactttt tttattgtg atatgggata     720 acctaggcat actgcactgt acactctgac atatgaagtg ctctagtcaa gtttaactgg    780
tgtccacaga ggacatggtt taactggaat tcgtcaagcc tctggttcta atttctcatt    840
tgcaggaaat gctggcatag agcagcacta atgacacca ctaaagaaac gatcagacag     900
atctggaatg tgaagcgtta tagaagataa ctggcctcat ttcttcaaaa tatcaagtgt    960
tgggaaagaa aaaaggaagt ggaatgggta actcttcttg attaaaagtt atgtaataac   1020
caaatgcaat gtgaaatatt ttactggact cttttgaaaa accatctgta aaagactgag   1080
gtgggggtgg gaggccagca cggtggtgag gcagttgaga aaatttgaat gtggattaga   1140
ttttgaatga tattggataa ttattggtaa tttatggcc tgtgagaagg gtgttgtagt    1200 ttataaaga ctgtcttaat ttgcatactt aagcatttag gaatgaagtg ttagagtgtc    1260
ttaaaatgtt tcaaatggtt taacaaaatg tatgtgaggc gtatgtggca aaatgttaca   1320
gaatctaact ggtggacatg gctgttcatt gtactgtttt tttctatctt ctatatgttt   1380
aaaagtatat aataaaaata tttaatttt                                     1408
```

<210> SEQ ID NO 12
<211> LENGTH: 1582
<212> TYPE: DNA
<213> ORGANISM: Homo sapiens

<400> SEQUENCE: 12

```
cggggcccca cgctgcgcat ccgcgggttt gctatggcga tgagcagcgg cggcagtggt     60
ggcggcgtcc cggagcagga ggattccgtg ctgttccggc gcggcacagg ccagagcgat    120
gattctgaca tttgggatga tacagcactg ataaaagcat atgataaagc tgtggcttca    180
tttaagcatg ctctaaagaa tggtgacatt tgtgaaactt cgggtaaacc aaaaaccaca    240
cctaaaagaa aacctgctaa gaagaataaa agccaaaaga gaatactgc agcttcctta    300 caacagtgga agttggggga caaatgttct gccatttggt cagaagacgg ttgcatttac    360
ccagctacca ttgcttcaat tgattttaag agagaaacct gtgttgtggt ttacactgga    420
tatgaaaata gagaggagca aaatctgtcc gatctacttt ccccaatctg tgaagtagct    480
aataatatag aacagaatgc tcaagagaat gaaaatgaaa gccaagtttc aacagatgaa    540
agtgagaact ccaggtctcc tggaaataaa tcagataaca tcaagcccaa atctgctcca    600
tggaactctt ttctccctcc accacccccc atgccagggc caagactggg accaggaaag    660
ccaggtctaa aattcaatgg cccaccaccg ccaccgccac caccaccacc ccacttacta    720
tcatgctggc tgcctccatt tccttctgga ccaccaataa ttcccccacc acctcccata    780
tgtccagatt ctcttgatga tgctgatgct ttggaagta tgttaatttc atggtacatg    840
agtggctatc atactggcta ttatatgggt ttcagacaaa atcaaaaaga aggaaggtgc    900
```

```
tcacattcct taaattaagg agaaatgctg gcatagagca gcactaaatg acaccactaa      960
agaaacgatc agacagatct ggaatgtgaa gcgttataga agataactgg cctcatttct     1020
tcaaaatatc aagtgttggg aaagaaaaaa ggaagtggaa tgggtaactc ttcttgatta     1080
aaagttatgt aataaccaaa tgcaatgtga aatattttac tggactcttt tgaaaaacca     1140
tctgtaaaag actggggtgg gggtgggagg ccagcacggt ggtgaggcag ttgagaaaat     1200
ttgaatgtgg attagatttt gaatgatatt ggataattat tggtaatttt atggcctgtg     1260
agaagggtgt tgtagtttat aaaagactgt cttaatttgc atacttaagc atttaggaat     1320
gaagtgttag agtgtcttaa aatgtttcaa atggtttaac aaaatgtatg tgaggcgtat     1380
gtggcaaaat gttacagaat ctaactggtg gacatggctg ttcattgtac tgtttttttc     1440
tatcttctat atgtttaaaa gtatataata aaaatattta atttttttt aaaaaaaaaa      1500 aaaaaaaaaa aaaaaaaaaa aaaaaaaaaa aaaaaaaaaa aaaaaaaaaa aaaaaaaaaa     1560
aaaaaaaaaa aaaaaaaaaa aa                                              1582

<210> SEQ ID NO 13
<211> LENGTH: 1408
<212> TYPE: DNA
<213> ORGANISM: Homo sapiens

<400> SEQUENCE: 13 aattttttaaa ttttttgtag agacagggtc tcattatgtt gcccagggtg gtgtcaagct      60
ccaggtctca agtgatcccc ctacctccgc ctcccaaagt tgtgggattg taggcatgag     120
ccactgcaag aaaaccttaa ctgcagccta ataattgttt tctttgggat aacttttaaa     180
gtacattaaa agactatcaa cttaatttct gatcatattt tgttgaataa aataagtaaa     240
atgtcttgtg aacaaaatgc tttttaacat ccatataaag ctatctatat atagctatct     300
atgtctatat agctattttt tttaacttcc ttttattttc cttacagggt ttcagacaaa     360
atcaaaaaga aggaaggtgc tcacattcct taaattaagg agtaagtctg ccagcattat     420
gaaagtgaat cttacttttg taaaacttta tggtttgtgg aaaacaaatg ttttttgaaca     480 gttaaaaagt tcagatgtta aaaagttgaa aggttaatgt aaaacaatca atattaaaga     540
attttgatgc caaaactatt agataaaagg ttaatctaca tccctactag aattctcata     600
cttaactggt tggttatgtg gaagaaacat actttcacaa taaagagctt taggatatga     660
tgccatttta tatcactagt aggcagacca gcagactttt ttttattgtg atatgggata     720
acctaggcat actgcactgt acactctgac atatgaagtg ctctagtcaa gtttaactgg     780
tgtccacaga ggacatggtt taactggaat tcgtcaagcc tctggttcta atttctcatt     840
tgcaggaaat gctggcatag agcagcacta aatgacacca ctaaagaaac gatcagacag     900
atctggaatg tgaagcgtta tagaagataa ctggcctcat tcttcaaaa tatcaagtgt     960 tgggaaagaa aaaggaagt ggaatgggta actcttcttg attaaaagtt atgtaataac    1020
caaatgcaat gtgaaatatt ttactggact cttttgaaaa accatctgta aaagactggg     1080
gtgggggtgg gaggccagca cggtggtgag gcagttgaga aaatttgaat gtggattaga     1140
ttttgaatga tattggataa ttattggtaa ttttatggcc tgtgagaagg gtgttgtagt     1200
ttataaaaga ctgtcttaat ttgcatactt aagcatttag gaatgaagtg ttagagtgtc     1260
ttaaaatgtt tcaaatggtt taacaaaatg tatgtgaggc gtatgtggca aaatgttaca     1320
gaatctaact ggtggacatg gctgttcatt gtactgtttt tttctatctt ctatatgttt     1380
aaaagtatat aataaaaata tttaatttt                                       1408
```

```
<210> SEQ ID NO 14
<211> LENGTH: 372
<212> TYPE: DNA
<213> ORGANISM: Artificial Sequence
<220> FEATURE:
<223> OTHER INFORMATION: C212 marker nucleotide sequence.
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t

<400> SEQUENCE: 14
acctganccc aganggtcaa ggctgcagtg agacgagatt gcnccactgc cctccaccct      60
gggtgataag agtgggaccc tgtntcaaaa catacacaca cacacacaca cacacacaca     120
cacacacaca cacactctct ctctctctct ctctctctct ctctctctct ctctctctca     180
aaaacacttg gtctgttatt tttncgaaat tgtcagtcat agttatctgt tagaccaaag     240
ctgngtaagn acatttatta cattgcctcc tacaacttca tcagctaatg tatttgctat     300
atagcaatta catatnggna tatattatct tnaggggatg gccangtnat aaaactgtca     360
ctgaggaaag ga                                                         372

<210> SEQ ID NO 15
<211> LENGTH: 294
<212> TYPE: DNA
<213> ORGANISM: Artificial Sequence
<220> FEATURE:
<223> OTHER INFORMATION: C272 marker nucleotide sequence.
```

```
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 15
cctcccacct nagcctcccc agtagctagg actataggcg tgcnccacca agctcagcta      60
tttttnntat ttagtagaga cggggtttcg gcangcttag gcctcgtntc gaactccagt     120
gtgtgtgtgt gtgtgtgtgt gtgtgtgtgt gtgtgtgtgt gtgtgtgtgt agatatttat     180 tcccctccc ccttggaaaa gtaagtaagc tcctactagg aatttaaaac ctgcttgatc      240
tatataaaga caaacaagga aagacaaaca tggggcagg aaggaaggca gatc            294

<210> SEQ ID NO 16
<211> LENGTH: 141
<212> TYPE: DNA
<213> ORGANISM: Artificial Sequence
<220> FEATURE:
<223> OTHER INFORMATION: C171 marker nucleotide sequence.

<400> SEQUENCE: 16
tcgaggtaga tttgtattat atcccatgta cacacacaca cacacacaca cacacacaca      60
cacacacaga cttaatctgt ttacagaaat aaaaggaata aaataccgtt tctactatac     120
accaaaacta gccatcttga c                                              141

<210> SEQ ID NO 17
<211> LENGTH: 305
<212> TYPE: DNA
<213> ORGANISM: Artificial Sequence
<220> FEATURE:
<223> OTHER INFORMATION: AFM157xd10 marker nucleotide sequence.

<400> SEQUENCE: 17
ccctgagaag gcttcctcct gagtatgcat aaacattcac agcttgcatg cgtgtgtgtg      60
tgtgtgtgtg tgtgtatgtt tgcttgcact gtaaaaacaa ttgcaacatc aacagaaata     120
aaaattaaag gaataattct cctccgactc tgccgttcca tccagtgaaa ctcttcattc     180
tggggtaaag ttccttcagt tctttcatag ataggtatat acttcataag tcaaacaatc     240
aggctgggtg cagtagctca tgcctgtaat cccagcccctt tgggaggccg agctgggcag    300
atcga                                                                305

<210> SEQ ID NO 18
<211> LENGTH: 350
<212> TYPE: DNA
<213> ORGANISM: Artificial Sequence
<220> FEATURE:
<223> OTHER INFORMATION: C161 marker nucleotide sequence.
<220> FEATURE:
<221> NAME/KEY: misc_feature
```

```
<222> LOCATION: (26)..(26)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t

<400> SEQUENCE: 18
tccacccgcc ttggcctccc aaagcnctgg gattacaggc gtgactgccg cacccagctg    60 taaactgggnt tnntaatggt agattttnag gtattaacaa tagataaaaa gatactttn   120 ggcatactgt gtattgggat ggggttagaa caggtgtnct acccaagaca tttacttaaa   180
atcgccctcg aaatgctatg tgagctgtgt gtgtgtgtgt gtgtgtgtgt gtattaagga   240
aaagcatgaa agtatttatg cttgattttt tttttnact catagcttca tagtgganca   300
gatacatagt ctaaatcaaa atgtttaaac tttttatgtc acttgctgtc               350

<210> SEQ ID NO 19
<211> LENGTH: 278
<212> TYPE: PRT
<213> ORGANISM: Homo sapiens

<400> SEQUENCE: 19

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
            20                  25                  30

Ile Trp Asp Asp Thr Ala Leu Ile Lys Ala Tyr Asp Lys Ala Val Ala
        35                  40                  45

Ser Phe Lys His Ala Leu Lys Asn Gly Asp Ile Cys Glu Thr Ser Gly
    50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110

Ile Ala Ser Ile Asp Phe Lys Arg Glu Thr Cys Val Val Val Tyr Thr
        115                 120                 125

Gly Tyr Gly Asn Arg Glu Glu Gln Asn Leu Ser Asp Leu Leu Ser Pro
    130                 135                 140
```

```
Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
        195                 200                 205

Lys Pro Gly Leu Lys Phe Asn Gly Pro Pro Pro Pro Pro Pro Pro
    210                 215                 220

Pro Pro His Leu Leu Ser Cys Trp Leu Pro Pro Phe Ser Gly Pro
225                 230                 235                 240

Pro Ile Ile Pro Pro Pro Ile Cys Pro Asp Ser Leu Asp Asp
            245                 250                 255

Ala Asp Ala Leu Gly Ser Met Leu Ile Ser Trp Tyr Met Ser Gly Tyr
            260                 265                 270

His Thr Gly Tyr Tyr Met
            275

<210> SEQ ID NO 20
<211> LENGTH: 885
<212> TYPE: DNA
<213> ORGANISM: Mouse
<220> FEATURE:
<221> NAME/KEY: CDS
<222> LOCATION: (18)..(881)

<400> SEQUENCE: 20
cggcgtggta gcaggcc atg gcg atg ggc agt ggc gga gcg ggc tcc gag              50
                   Met Ala Met Gly Ser Gly Gly Ala Gly Ser Glu
                    1               5                  10 cag gaa gat acg gtg ctg ttc cgg cgt ggc acc ggc cag agt gat gat             98
Gln Glu Asp Thr Val Leu Phe Arg Arg Gly Thr Gly Gln Ser Asp Asp
            15                  20                  25 tct gac att tgg gat gat aca gca ttg ata aaa gct tat gat aaa gct            146
Ser Asp Ile Trp Asp Asp Thr Ala Leu Ile Lys Ala Tyr Asp Lys Ala
        30                  35                  40 gtg gct tcc ttt aag cat gct cta aag aac ggt gac att tgt gaa act            194
Val Ala Ser Phe Lys His Ala Leu Lys Asn Gly Asp Ile Cys Glu Thr
    45                  50                  55 cca gat aag cca aaa ggc aca gcc aga aga aaa cct gcc aag aag aat            242
Pro Asp Lys Pro Lys Gly Thr Ala Arg Arg Lys Pro Ala Lys Lys Asn
60                  65                  70                  75 aaa agc caa aag aag aat gcc aca act ccc ttg aaa cag tgg aaa gtt            290
Lys Ser Gln Lys Lys Asn Ala Thr Thr Pro Leu Lys Gln Trp Lys Val
                80                  85                  90 ggt gac aag tgt tct gct gtt tgg tca gaa gac ggc tgc att tac cca            338
Gly Asp Lys Cys Ser Ala Val Trp Ser Glu Asp Gly Cys Ile Tyr Pro
            95                  100                 105 gct act att acg tcc att gac ttt aag aga gaa acc tgt gtc gtg gtt            386
Ala Thr Ile Thr Ser Ile Asp Phe Lys Arg Glu Thr Cys Val Val Val
        110                 115                 120 tat act gga tat gga aac aga gag gag caa aac tta tct gac cta ctt            434
Tyr Thr Gly Tyr Gly Asn Arg Glu Glu Gln Asn Leu Ser Asp Leu Leu
    125                 130                 135 tcc ccg acc tgt gaa gta gct aat agt aca gaa cag aac act cag gag            482
Ser Pro Thr Cys Glu Val Ala Asn Ser Thr Glu Gln Asn Thr Gln Glu
140                 145                 150                 155 aat gaa agt caa gtt tcc aca gac gac agt gaa cac tcc tcc aga tcg            530
Asn Glu Ser Gln Val Ser Thr Asp Asp Ser Glu His Ser Ser Arg Ser
```

```
                     160                 165                 170
ctc aga agt aaa gca cac agc aag tcc aaa gct gct ccg tgg acc tca      578
Leu Arg Ser Lys Ala His Ser Lys Ser Lys Ala Ala Pro Trp Thr Ser
        175                 180                 185 ttt ctt cct cca cca ccc cca atg cca ggg tca gga tta gga cca gga      626
Phe Leu Pro Pro Pro Pro Pro Met Pro Gly Ser Gly Leu Gly Pro Gly
190                 195                 200 aag cca ggt cta aaa ttc aac ggc ccg ccg ccg cct cca cta ccc          674
Lys Pro Gly Leu Lys Phe Asn Gly Pro Pro Pro Pro Pro Leu Pro
    205                 210                 215 cct ccc ccc ttc ctg ccg tgc tgg atg ccc cgg ttc cct tca gga cca      722
Pro Pro Pro Phe Leu Pro Cys Trp Met Pro Arg Phe Pro Ser Gly Pro
220                 225                 230                 235 cca ata atc ccg cca ccc cct ccc atc tct ccc gac tgt ctg gat gac      770
Pro Ile Ile Pro Pro Pro Pro Pro Ile Ser Pro Asp Cys Leu Asp Asp
                240                 245                 250 act gat gcc ctg ggc agt atg cta atc tct tgg tac atg agt ggc tac      818
Thr Asp Ala Leu Gly Ser Met Leu Ile Ser Trp Tyr Met Ser Gly Tyr
                255                 260                 265 cac act ggc tac tat atg ggt ttc aga caa aat aaa aaa gaa gga aag      866
His Thr Gly Tyr Tyr Met Gly Phe Arg Gln Asn Lys Lys Glu Gly Lys
        270                 275                 280 tgc tca cat aca aat taag                                              885
Cys Ser His Thr Asn
    285

<210> SEQ ID NO 21
<211> LENGTH: 288
<212> TYPE: PRT
<213> ORGANISM: Mouse

<400> SEQUENCE: 21

Met Ala Met Gly Ser Gly Ala Gly Ser Glu Gln Glu Asp Thr Val
1               5                   10                  15

Leu Phe Arg Arg Gly Thr Gly Gln Ser Asp Asp Ser Asp Ile Trp Asp
                20                  25                  30

Asp Thr Ala Leu Ile Lys Ala Tyr Asp Lys Ala Val Ala Ser Phe Lys
            35                  40                  45

His Ala Leu Lys Asn Gly Asp Ile Cys Glu Thr Pro Asp Lys Pro Lys
        50                  55                  60

Gly Thr Ala Arg Arg Lys Pro Ala Lys Lys Asn Lys Ser Gln Lys Lys
65                  70                  75                  80

Asn Ala Thr Thr Pro Leu Lys Gln Trp Lys Val Gly Asp Lys Cys Ser
                85                  90                  95

Ala Val Trp Ser Glu Asp Gly Cys Ile Tyr Pro Ala Thr Ile Thr Ser
            100                 105                 110

Ile Asp Phe Lys Arg Glu Thr Cys Val Val Tyr Thr Gly Tyr Gly
        115                 120                 125

Asn Arg Glu Glu Gln Asn Leu Ser Asp Leu Leu Ser Pro Thr Cys Glu
    130                 135                 140

Val Ala Asn Ser Thr Glu Gln Asn Thr Gln Asn Glu Ser Gln Val
145                 150                 155                 160

Ser Thr Asp Asp Ser Glu His Ser Ser Arg Ser Leu Arg Ser Lys Ala
                165                 170                 175

His Ser Lys Ser Lys Ala Ala Pro Trp Thr Ser Phe Leu Pro Pro Pro
            180                 185                 190

Pro Pro Met Pro Gly Ser Gly Leu Gly Pro Gly Lys Pro Gly Leu Lys
        195                 200                 205
```

```
Phe Asn Gly Pro Pro Pro Pro Pro Leu Pro Pro Pro Phe Leu
    210                 215                 220

Pro Cys Trp Met Pro Pro Phe Pro Ser Gly Pro Pro Ile Ile Pro Pro
225             230                 235                 240

Pro Pro Pro Ile Ser Pro Asp Cys Leu Asp Asp Thr Asp Ala Leu Gly
                245                 250                 255

Ser Met Leu Ile Ser Trp Tyr Met Ser Gly Tyr His Thr Gly Tyr Tyr
        260                 265                 270

Met Gly Phe Arg Gln Asn Lys Lys Glu Gly Lys Cys Ser His Thr Asn
        275                 280                 285

<210> SEQ ID NO 22
<211> LENGTH: 3271
<212> TYPE: DNA
<213> ORGANISM: Homo sapiens
<220> FEATURE:
<221> NAME/KEY: CDS
<222> LOCATION: (104)..(184)
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: CDS
<222> LOCATION: (364)..(435)
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: CDS
<222> LOCATION: (637)..(756)
<220> FEATURE:
<221> NAME/KEY: CDS
<222> LOCATION: (921)..(1121)
<220> FEATURE:
<221> NAME/KEY: CDS
<222> LOCATION: (1265)..(1417)
<220> FEATURE:
<221> NAME/KEY: CDS
<222> LOCATION: (1605)..(1700)
<220> FEATURE:
<221> NAME/KEY: CDS
<222> LOCATION: (1810)..(1920)
<220> FEATURE:
<221> NAME/KEY: CDS
<222> LOCATION: (2214)..(2261)

<400> SEQUENCE: 22
cctcccgggc accgtactgt tccgctccca gaagccccgg gcgccggaag tcgtcactct      60
taagaaggga cggggcccca cgctgcgcac ccgcgggttt gct atg gcg atg agc     115
                                              Met Ala Met Ser
                                                1 agc ggc ggc agt ggt ggc ggc gtc ccg gag cag gag gat tcc gtg ctg     163
Ser Gly Gly Ser Gly Gly Gly Val Pro Glu Gln Glu Asp Ser Val Leu
 5              10                  15                  20 ttc cgg cgc ggc aca ggc cag gtgaggtcgc agccagtgca gtctccctat         214
Phe Arg Arg Gly Thr Gly Gln
                25 tagcgctctc agcacccttc ttccggccca actctccttc cgcagtgtaa ttttgttatg    274 tgtggattaa gatgactctt ggtactaaca tacattttct gattaaacct atctgnacat    334 gagttgtttt tatttcttac cctttccag agc gat gat tct gac att tgg gat     387
                                Ser Asp Asp Ser Asp Ile Trp Asp
                                                30              35 gat aca gca ctg ata aaa gca tat gat aaa gct gtg gct tca ttt aag     435
Asp Thr Ala Leu Ile Lys Ala Tyr Asp Lys Ala Val Ala Ser Phe Lys
```

```
                    40          45          50
gtatgaaatg cttgnttagt cgttttctta ttttctcgtt attcatttgg aaaggaattg    495
ataacatacg ataaagtgtt aaggtgcttt tctgaggtga cggagccttg agactagctt    555
atagtagtaa ctgggttatg tcgtgacttt tattctgtgc accaccctgt aacatgtaca    615
tttttattcc tattttcgta g cat gct cta aag aat ggt gac att tgt gaa     666
                         His Ala Leu Lys Asn Gly Asp Ile Cys Glu
                                      55                  60 act tcg ggt aaa cca aaa acc aca cct aaa aga aaa cct gct aag aag     714
Thr Ser Gly Lys Pro Lys Thr Thr Pro Lys Arg Lys Pro Ala Lys Lys
             65                  70                  75 aat aaa agc caa aag aag aat act gca gct tcc tta caa cag             756
Asn Lys Ser Gln Lys Lys Asn Thr Ala Ala Ser Leu Gln Gln
         80                  85                  90 gttattttaa aatgttgagg atttaacttc aaaggatgtc tcattagtcc ttatttaata   816
gtgtaaaatg tctttaactg cctgcaggtc gatcaaaacg atgatagt ttgccctctt     876 caaaagaaat gtgtgcatgt atatatcttt gatttctttt gtag tgg aaa gtt ggg    932
                                                Trp Lys Val Gly
                                                             95 gac aaa tgt tct gcc att tgg tca gaa gac ggt tgc att tac cca gct     980
Asp Lys Cys Ser Ala Ile Trp Ser Glu Asp Gly Cys Ile Tyr Pro Ala
             100                 105                 110 acc att gct tca att gat ttt aag aga gaa acc tgt gtt gtg gtt tac    1028
Thr Ile Ala Ser Ile Asp Phe Lys Arg Glu Thr Cys Val Val Val Tyr
             115                 120                 125 act gga tat gga aat aga gag gag caa aat ctg tcc gat cta ctt tcc    1076
Thr Gly Tyr Gly Asn Arg Glu Glu Gln Asn Leu Ser Asp Leu Leu Ser
             130                 135                 140 cca atc tgt gaa gta gct aat aat ata gaa cag aat gct caa gag        1121
Pro Ile Cys Glu Val Ala Asn Asn Ile Glu Gln Asn Ala Gln Glu
             145                 150                 155 gtaaggatac aaaaaaaaaa aaattcaatt tctggaagca gagactagat gagaaactgt   1181
taaacagtat acaccaccga ggcattaatt ttttcttaat cacacccta taacaaaaac    1241 ctgcatattt ttctttttta aag aat gaa aat gaa agc caa gtt tca aca gat  1294
                       Asn Glu Asn Glu Ser Gln Val Ser Thr Asp
                                    160                 165 gaa agt gag aac tcc agg tct cct gga aat aaa tca gat aac atc aag    1342
Glu Ser Glu Asn Ser Arg Ser Pro Gly Asn Lys Ser Asp Asn Ile Lys
             170                 175                 180 ccc aaa tct gct cca tgg aac tct ttt ctc cct cca cca ccc ccc atg    1390
Pro Lys Ser Ala Pro Trp Asn Ser Phe Leu Pro Pro Pro Pro Pro Met
185                  190                 195                 200 cca ggg cca aga ctg gga cca gga aag gtaaaccttc tatgaaagtt          1437
Pro Gly Pro Arg Leu Gly Pro Gly Lys
             205 ttccagaaaa tagttaatgt cgggacattt aacctctctg ttaactaatt tgtagctctc   1497 ccacaaatat tctgggtaat tatttttatc cttttggttt tgagtccttt ttattcctat   1557 catattgaaa ttggtaagtt aattttcctt tgaaatattc cttatag cca ggt cta    1613
                                                    Pro Gly Leu
                                                            210 aaa ttc aat ggc cca cca ccg cca ccg cca cca cca ccc cac tta        1661
Lys Phe Asn Gly Pro Pro Pro Pro Pro Pro Pro Pro Pro His Leu
             215                 220                 225 cta tca tgc tgg ctg cct cca ttt cct tct gga cca cca gtaagtaaaa     1710
Leu Ser Cys Trp Leu Pro Pro Phe Pro Ser Gly Pro Pro
             230                 235                 240
```

-continued

```
aagagtatag gttagatttt gctttcacat acaatttgat aattaccaga ctttactttt      1770
tgtttactgg atataaacaa tatcttttc tgtctccag ata att ccc cca cca          1824
                                           Ile Ile Pro Pro Pro
                                                         245 cct ccc ata tgt cca gat tct ctt gat gat gct gat gct ttg gga agt       1872
Pro Pro Ile Cys Pro Asp Ser Leu Asp Asp Ala Asp Ala Leu Gly Ser
            250             255             260 atg tta att tca tgg tac atg agt ggc tat cat act ggc tat tat atg       1920
Met Leu Ile Ser Trp Tyr Met Ser Gly Tyr His Thr Gly Tyr Tyr Met
        265             270             275 gtaagtaatc actcagcatc ttttcctgac aattttttg tagttatgtg actttgtttg       1980
gtaaatttat aaaatactac ttgaactgca gcctaataat tgttttcttt gggataactt      2040
ttaaagtaca ttaaaagact atcaacttaa tttctgatca tattttgttg aataaaataa     2100
gtaaaatgtc ttgtgaaaca aaatgctttt taacatccat ataaagctat ctatatatag     2160
ctatctatgt ctatatagct atttttttta acttccttt attttcctta cag ggt         2216
                                                            Gly ttc aga caa aat caa aaa gaa gga agg tgc tca cat tcc tta aat            2261
Phe Arg Gln Asn Gln Lys Glu Gly Arg Cys Ser His Ser Leu Asn
280             285             290 taaggagtaa gtctgccagc attatgaaag tgaatcttac ttttgtaaaa ctttatggtt     2321
tgtggaaaac aaatgttttt gaacagttaa aaagttcaga tgttaaaaag ttgaaaggtt     2381
aatgtaaaac aatcaatatt aaagaatttt gatgccaaaa ctattagata aaggttaat      2441 ctacatccct actagaattc tcatacttaa ctggttggtt atgtggaaga aacatacttt    2501
cacaataaag agctttagga tatgatgcca ttttatatca ctagtaggca gaccagcaga    2561 cttttttta ttgtgatatg ggataaccta ggcatactgc actgtacact ctgacatatg      2621
aagtgctcta gtcaagttta actggtgtcc acagaggaca tggtttaact ggaattcgtc    2681
aagcctctgg ttctaatttc tcatttgcag gaaatgctgg catagagcag cactaaatga    2741
caccactaaa gaaacgatca gacagatctg gaatgtgaag cgttatagaa gataactggc    2801
ctcatttctt caaatatca agtgttggga agaaaaaag gaagtggaat gggtaactct      2861
tcttgattaa aagttatgta ataaccaaat gcaatgtgaa atattttact ggactctttt    2921
gaaaaaccat ctagtaaaag actggggtgg ggtggggagg ccagcacggt ggtgaggcag    2981
ttgagaaaat ttgaatgtgg attagatttt gaatgatatt ggataattat tggtaatttt   3041
atggcctgtg agaagggtgt tgtagtttat aaaagactgt cttaatttgc atacttaagc   3101
atttaggaat gaagtgttag agtgtcttaa aatgtttcaa atggtttaac aaaatgtatg   3161
tgaggcgtat gtggcaaaat gttacagaat ctaactggtg gacatggctg ttcattgtac   3221 tgttttttc tatcttctat atgtttaaaa gtatataata aaaatattta               3271
```

<210> SEQ ID NO 23
<211> LENGTH: 637
<212> TYPE: DNA
<213> ORGANISM: Homo sapiens
<220> FEATURE:
<221> NAME/KEY: CDS
<222> LOCATION: (608)..(637)

<400> SEQUENCE: 23

```
gatctgcctt ccttcctgcc cccatgtttg tctttccttg tttgtcttta tatagatcaa      60
gcaggtttta aattcctagt aggagcttac atttactttt ccaaggggga ggggaataa      120 atatctacac acacacacac acacacacca cactggagtt cgagacgagg cctaagcaac    180
```

```
atgccgaaac cccgtctcta ctaaatacaa aaatagctg agcttggtgg cgcacgccta    240
tagtcctagc tactggggag gctgaggtgg gaggatcgct tgagcccaag aagtcgaggc    300
tgcagtgagc cgagatcgcg ccgctgcact ccagcctgag cgacagggcg aggctctgtc    360
tcaaaacaaa caaacaaaaa aaaaaaggaa aggaaatata acacagtgaa atgaaaggat    420
tgagagaaat gaaaaatata cacgccacaa atgtgggagg gcgataacca ctcgtagaaa    480
gcgtgagaag ttactacaag cggtcctccc gggcaccgta ctgttccgct cccgaaagcc    540
ccgggcgccg gaagtcgtca ctcttaagaa gggacggggc cccacgctgc gcacccgcgg    600 gttttgct atg gcg atg agc agc ggc ggc agt ggt ggc                    637
         Met Ala Met Ser Ser Gly Gly Ser Gly Gly
           1               5                  10
```

<210> SEQ ID NO 24
<211> LENGTH: 19
<212> TYPE: DNA
<213> ORGANISM: Homo sapiens

<400> SEQUENCE: 24
agggcgaggc tctgtctca                                                19

<210> SEQ ID NO 25
<211> LENGTH: 19
<212> TYPE: DNA
<213> ORGANISM: Homo sapiens

<400> SEQUENCE: 25
cgggaggacc gcttgtagt                                                19

<210> SEQ ID NO 26
<211> LENGTH: 19
<212> TYPE: DNA
<213> ORGANISM: Homo sapiens

<400> SEQUENCE: 26
gccggaagtc gtcactctt                                                19

<210> SEQ ID NO 27
<211> LENGTH: 20
<212> TYPE: DNA
<213> ORGANISM: Homo sapiens

<400> SEQUENCE: 27
gggtgctgag agcgctaata                                               20

<210> SEQ ID NO 28
<211> LENGTH: 20
<212> TYPE: DNA
<213> ORGANISM: Homo sapiens

<400> SEQUENCE: 28
tgtgtggatt aagatgactc                                               20

<210> SEQ ID NO 29
<211> LENGTH: 19
<212> TYPE: DNA
<213> ORGANISM: Homo sapiens

<400> SEQUENCE: 29
cactttatcg tatgttatc                                                19

<210> SEQ ID NO 30

```
<211> LENGTH: 22
<212> TYPE: DNA
<213> ORGANISM: Homo sapiens

<400> SEQUENCE: 30
ctgtgcacca ccctgtaaca tg                                              22

<210> SEQ ID NO 31
<211> LENGTH: 19
<212> TYPE: DNA
<213> ORGANISM: Homo sapiens

<400> SEQUENCE: 31
aaggactaat gagacatcc                                                  19

<210> SEQ ID NO 32
<211> LENGTH: 20
<212> TYPE: DNA
<213> ORGANISM: Homo sapiens

<400> SEQUENCE: 32
cgagatgata gtttgccctc                                                 20

<210> SEQ ID NO 33
<211> LENGTH: 24
<212> TYPE: DNA
<213> ORGANISM: Homo sapiens

<400> SEQUENCE: 33
agctacttca cagattgggg aaag                                            24

<210> SEQ ID NO 34
<211> LENGTH: 20
<212> TYPE: DNA
<213> ORGANISM: Homo sapiens

<400> SEQUENCE: 34
ctcatctagt ctctgcttcc                                                 20

<210> SEQ ID NO 35
<211> LENGTH: 24
<212> TYPE: DNA
<213> ORGANISM: Homo sapiens

<400> SEQUENCE: 35
tggatatgga aatagagagg gagc                                            24

<210> SEQ ID NO 36
<211> LENGTH: 22
<212> TYPE: DNA
<213> ORGANISM: Homo sapiens

<400> SEQUENCE: 36 caccttata acaaaaacct gc                                               22

<210> SEQ ID NO 37
<211> LENGTH: 23
<212> TYPE: DNA
<213> ORGANISM: Homo sapiens

<400> SEQUENCE: 37
gagaaaggag ttccatggag cag                                             23

<210> SEQ ID NO 38
```

```
<211> LENGTH: 20
<212> TYPE: DNA
<213> ORGANISM: Homo sapiens

<400> SEQUENCE: 38
gagaggttaa atgtcccgac                                              20

<210> SEQ ID NO 39
<211> LENGTH: 22
<212> TYPE: DNA
<213> ORGANISM: Homo sapiens

<400> SEQUENCE: 39
gtgagaactc caggtctcct gg                                           22

<210> SEQ ID NO 40
<211> LENGTH: 20
<212> TYPE: DNA
<213> ORGANISM: Homo sapiens

<400> SEQUENCE: 40
tgagtctgtt tgacttcagg                                              20

<210> SEQ ID NO 41
<211> LENGTH: 22
<212> TYPE: DNA
<213> ORGANISM: Homo sapiens

<400> SEQUENCE: 41
gaaggaaatg gaggcagcca gc                                           22

<210> SEQ ID NO 42
<211> LENGTH: 21
<212> TYPE: DNA
<213> ORGANISM: Homo sapiens

<400> SEQUENCE: 42
tttctaccca ttagaatctg g                                            21

<210> SEQ ID NO 43
<211> LENGTH: 24
<212> TYPE: DNA
<213> ORGANISM: Homo sapiens

<400> SEQUENCE: 43
ccccacttac tatcatgctg gctg                                         24

<210> SEQ ID NO 44
<211> LENGTH: 24
<212> TYPE: DNA
<213> ORGANISM: Homo sapiens

<400> SEQUENCE: 44
ccagacttta cttttttgttt actg                                        24

<210> SEQ ID NO 45
<211> LENGTH: 21
<212> TYPE: DNA
<213> ORGANISM: Homo sapiens

<400> SEQUENCE: 45
atagccactc atgtaccatg a                                            21

<210> SEQ ID NO 46
```

```
<211> LENGTH: 24
<212> TYPE: DNA
<213> ORGANISM: Homo sapiens

<400> SEQUENCE: 46
aagagtaatt taagcctcag acag                                              24

<210> SEQ ID NO 47
<211> LENGTH: 24
<212> TYPE: DNA
<213> ORGANISM: Homo sapiens

<400> SEQUENCE: 47
ctcccatatg tccagattct cttg                                              24

<210> SEQ ID NO 48
<211> LENGTH: 25
<212> TYPE: DNA
<213> ORGANISM: Homo sapiens

<400> SEQUENCE: 48
agactatcaa cttaatttct gatca                                             25

<210> SEQ ID NO 49
<211> LENGTH: 24
<212> TYPE: DNA
<213> ORGANISM: Homo sapiens

<400> SEQUENCE: 49
taaggaatgt gagcaccttc cttc                                              24

<210> SEQ ID NO 50
<211> LENGTH: 25
<212> TYPE: DNA
<213> ORGANISM: Homo sapiens

<400> SEQUENCE: 50
agactatcaa cttaatttct gatca                                             25

<210> SEQ ID NO 51
<211> LENGTH: 24
<212> TYPE: DNA
<213> ORGANISM: Homo sapiens

<400> SEQUENCE: 51
gtaagattca ctttcataat gctg                                              24

<210> SEQ ID NO 52
<211> LENGTH: 21
<212> TYPE: DNA
<213> ORGANISM: Homo sapiens

<400> SEQUENCE: 52
ctttatggtt tgtggaaaac a                                                 21

<210> SEQ ID NO 53
<211> LENGTH: 20
<212> TYPE: DNA
<213> ORGANISM: Homo sapiens

<400> SEQUENCE: 53
ggcatcatat cctaaagctc                                                   20

<210> SEQ ID NO 54
```

-continued

<211> LENGTH: 23
<212> TYPE: DNA
<213> ORGANISM: Homo sapiens

<400> SEQUENCE: 54
gtaataacca aatgcaatgt gaa                                           23

<210> SEQ ID NO 55
<211> LENGTH: 20
<212> TYPE: DNA
<213> ORGANISM: Homo sapiens

<400> SEQUENCE: 55
ctacaacacc cttctcacag                                               20

<210> SEQ ID NO 56
<211> LENGTH: 20
<212> TYPE: DNA
<213> ORGANISM: Homo sapiens

<400> SEQUENCE: 56
ggtgtccaca gaggacatgg                                               20

<210> SEQ ID NO 57
<211> LENGTH: 24
<212> TYPE: DNA
<213> ORGANISM: Homo sapiens

<400> SEQUENCE: 57
aagagttaac ccattccagc ttcc                                          24

<210> SEQ ID NO 58
<211> LENGTH: 27
<212> TYPE: PRT
<213> ORGANISM: Homo sapiens

<400> SEQUENCE: 58

Met Ala Met Ser Ser Gly Gly Ser Gly Gly Gly Val Pro Glu Gln Glu
1               5                   10                  15

Asp Ser Val Leu Phe Arg Arg Gly Thr Gly Gln
            20                  25

<210> SEQ ID NO 59
<211> LENGTH: 24
<212> TYPE: PRT
<213> ORGANISM: Homo sapiens

<400> SEQUENCE: 59

Ser Asp Asp Ser Asp Ile Trp Asp Asp Thr Ala Leu Ile Lys Ala Tyr
1               5                   10                  15

Asp Lys Ala Val Ala Ser Phe Lys
            20

<210> SEQ ID NO 60
<211> LENGTH: 40
<212> TYPE: PRT
<213> ORGANISM: Homo sapiens

<400> SEQUENCE: 60

His Ala Leu Lys Asn Gly Asp Ile Cys Glu Thr Ser Gly Lys Pro Lys
1               5                   10                  15

Thr Thr Pro Lys Arg Lys Pro Ala Lys Lys Asn Lys Ser Gln Lys Lys
            20                  25                  30

```
Asn Thr Ala Ala Ser Leu Gln Gln
         35                  40
```

```
<210> SEQ ID NO 61
<211> LENGTH: 67
<212> TYPE: PRT
<213> ORGANISM: Homo sapiens

<400> SEQUENCE: 61

Trp Lys Val Gly Asp Lys Cys Ser Ala Ile Trp Ser Glu Asp Gly Cys
1               5                   10                  15

Ile Tyr Pro Ala Thr Ile Ala Ser Ile Asp Phe Lys Arg Glu Thr Cys
            20                  25                  30

Val Val Val Tyr Thr Gly Tyr Gly Asn Arg Glu Glu Gln Asn Leu Ser
         35                  40                  45

Asp Leu Leu Ser Pro Ile Cys Glu Val Ala Asn Asn Ile Glu Gln Asn
     50                  55                  60

Ala Gln Glu
65
```

```
<210> SEQ ID NO 62
<211> LENGTH: 51
<212> TYPE: PRT
<213> ORGANISM: Homo sapiens

<400> SEQUENCE: 62

Asn Glu Asn Glu Ser Gln Val Ser Thr Asp Glu Ser Glu Asn Ser Arg
1               5                   10                  15

Ser Pro Gly Asn Lys Ser Asp Asn Ile Lys Pro Lys Ser Ala Pro Trp
            20                  25                  30

Asn Ser Phe Leu Pro Pro Pro Pro Met Pro Gly Pro Arg Leu Gly
         35                  40                  45

Pro Gly Lys
     50
```

```
<210> SEQ ID NO 63
<211> LENGTH: 32
<212> TYPE: PRT
<213> ORGANISM: Homo sapiens

<400> SEQUENCE: 63

Pro Gly Leu Lys Phe Asn Gly Pro Pro Pro Pro Pro Pro Pro Pro Pro
1               5                   10                  15

Pro His Leu Leu Ser Cys Trp Leu Pro Pro Phe Pro Ser Gly Pro Pro
            20                  25                  30
```

```
<210> SEQ ID NO 64
<211> LENGTH: 37
<212> TYPE: PRT
<213> ORGANISM: Homo sapiens

<400> SEQUENCE: 64

Ile Ile Pro Pro Pro Pro Pro Ile Cys Pro Asp Ser Leu Asp Asp Ala
1               5                   10                  15

Asp Ala Leu Gly Ser Met Leu Ile Ser Trp Tyr Met Ser Gly Tyr His
            20                  25                  30

Thr Gly Tyr Tyr Met
         35
```

```
<210> SEQ ID NO 65
<211> LENGTH: 16
```

```
<212> TYPE: PRT
<213> ORGANISM: Homo sapiens

<400> SEQUENCE: 65

Gly Phe Arg Gln Asn Gln Lys Glu Gly Arg Cys Ser His Ser Leu Asn
1               5                   10                  15
```